United States Patent
Nagato et al.

(10) Patent No.: US 10,562,862 B2
(45) Date of Patent: Feb. 18, 2020

(54) METHOD FOR MANUFACTURING NITROGEN-CONTAINING HETEROCYCLIC COMPOUND AND INTERMEDIATE OF SAME

(71) Applicant: FUJIFILM Corporation, Minato-ku, Tokyo (JP)

(72) Inventors: Yusuke Nagato, Toyama (JP); Shinsuke Mizumoto, Toyama (JP); Tatsuya Murakami, Toyama (JP); Tomoyuki Tanaka, Toyama (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/272,263

(22) Filed: Feb. 11, 2019

(65) Prior Publication Data

US 2019/0169133 A1 Jun. 6, 2019

Related U.S. Application Data

(60) Division of application No. 15/867,122, filed on Jan. 10, 2018, now Pat. No. 10,435,377, which is a continuation of application No. PCT/JP2016/070758, filed on Jul. 14, 2016.

(30) Foreign Application Priority Data

Jul. 15, 2015 (JP) ................................ 2015-141034

(51) Int. Cl.
*C07D 239/48* (2006.01)
*C07D 403/06* (2006.01)
*A61K 31/505* (2006.01)

(52) U.S. Cl.
CPC ......... *C07D 239/48* (2013.01); *C07D 403/06* (2013.01); *A61K 31/505* (2013.01)

(58) Field of Classification Search
CPC ........................... C07D 239/48; C07D 403/06
See application file for complete search history.

(56) References Cited

U.S. PATENT DOCUMENTS

| | | | |
|---|---|---|---|
| 8,703,767 B2 | 4/2014 | Bearss et al. | |
| 9,145,415 B2 | 9/2015 | Takasaki et al. | |
| 9,701,644 B2 | 7/2017 | Mizumoto et al. | |
| 2003/0171359 A1 | 9/2003 | Dahmann et al. | |
| 2012/0035168 A1 | 2/2012 | Brandl et al. | |
| 2012/0149722 A1 | 6/2012 | Lee et al. | |
| 2012/0225436 A1 | 9/2012 | Fernandez-Salas et al. | |
| 2013/0059847 A1 | 3/2013 | Bearss et al. | |
| 2015/0045339 A1 | 2/2015 | Takasaki et al. | |
| 2016/0229812 A1 | 8/2016 | Mizumoto et al. | |
| 2017/0165262 A1 | 6/2017 | Naoe et al. | |

FOREIGN PATENT DOCUMENTS

| | | |
|---|---|---|
| CN | 102105150 A | 6/2011 |
| EP | 2 840 080 A1 | 2/2015 |
| JP | 2009-515851 A | 4/2009 |
| WO | 91/09856 A1 | 7/1991 |
| WO | 2006/133426 A2 | 12/2006 |
| WO | 2006/135713 A2 | 12/2006 |
| WO | 2007/054550 A1 | 5/2007 |
| WO | 2007/109120 A2 | 9/2007 |
| WO | 2009/095399 A2 | 8/2009 |
| WO | 2010/129053 A2 | 11/2010 |
| WO | 2012/061303 A1 | 5/2012 |
| WO | 2012/064706 A1 | 5/2012 |
| WO | 2012/135801 A1 | 10/2012 |
| WO | 2012/150952 A1 | 11/2012 |
| WO | 2013/157540 A1 | 10/2013 |
| WO | 2015/056683 A1 | 4/2015 |
| WO | 2016/027904 A1 | 2/2016 |

OTHER PUBLICATIONS

Office Action dated May 21, 2019, issued by the India Patent Office in corresponding Indian Application No. 201847001431.
Keith W. Pratz et al., "FLT3-mutant allelic burden and clinical status are predictive of response to FLT3 inhibitors in AML", Blood, Feb. 18, 2010, vol. 115, No. 7, pp. 1425-1432 (9 pgs. total).
D. Gary Gilliland et al., "The roles of FLT3 in hematopoiesis and leukemia", Blood, Sep. 1, 2002, vol. 100, No. 5, pp. 1532-1542 (12 pgs. total).
P. Brown et al., "FLT3 Inhibitors: a paradigm for the development of targeted therapeutics for paediatric cancer", European Journal of Cancer, 2004, vol. 40, pp. 707-721 (18 pgs. total).
American Cancer Society, "Cancer Facts & Figures 2012", 2012, pp. 9-24 (68 pgs. total).
S. Yokota et al., "Internal tandem duplication of the FLT3 gene is preferentially seen in acute myeloid leukemia and myelodysplastic syndrome among various hematological malignancies. A study on a large series of patients and cell lines", Leukemia, 1997, vol. 11, pp. 1605-1609.

(Continued)

*Primary Examiner* — Susanna Moore
(74) *Attorney, Agent, or Firm* — Sughrue Mion, PLLC

(57) ABSTRACT

An object of the present invention is to provide a method for industrially manufacturing a nitrogen-containing heterocyclic compound which shows excellent FLT3 inhibitory activity and is useful as a pharmaceutical active ingredient of pharmaceutical products. The present invention provides a manufacturing method of a compound represented by General Formula [14] or a salt thereof (in the formula, $R^1$ represents a $C_{1-6}$ alkyl group which may be substituted; and $R^8$ represents a leaving group or the like).

[14]

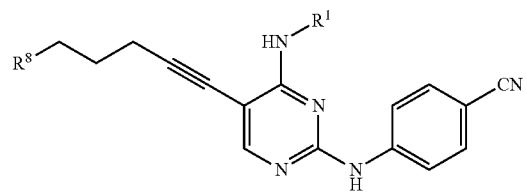

3 Claims, No Drawings

(56) References Cited

OTHER PUBLICATIONS

Chunaram Choudhary et al., "AML-associated Flt3 kinase domain mutations show signal transduction differences compared with Flt3 ITD mutations", Blood, Jul. 1, 2005, vol. 106, No. 1, pp. 265-273.
Hitoshi Kiyoi et al., "Mechanism of constitutive activation of FLT3 with internal tandem duplication in the juxtamembrane domain", Oncogene, 2002, vol. 21, pp. 2555-2563.
CAS Registry Nos. 1208542-16-8; 1211912-67-2; and 1370823-68-9, 2010, (2 pgs. Total).
Jacques H. Poupaert, "Drug Design: Basic Principles and Applications", in 2 Encyclopedia of Pharmaceutical Technology, James Swarbrick ed., 3rd ed., 2007, pp. 1362-1370.
Bruce A. Chabner et al., "Chemotherapy of Neoplastic Diseases; Antineoplastic Agents," Goodman & Gilman's: The Pharmacological Basis of Therapeutics, Chapter 51, L.L. Brunton et al., eds., 11th ed., 2006, pp. 1315-1403 (93 pgs. total).
Jan Cools et al., Prediction of Resistance to Small Molecule FLT3 Inhibitors: Implications for Molecularly Targeted Therapy of Acute Leukemia, Cancer Research, vol. 64, Sep. 15, 2004, pp. 6385-6389 (6 pgs. total).
Andrica C.H. de Vries et al., "Role of mutation independent constitutive activation of FLT3 in juvenile myelomonocytic leukemia", Haematologica, 2007, vol. 92, No. 11, pp. 1557-1560.
International Search Report dated Oct. 13, 2015, issued by the International Searching Authority in Application No. PCT/JP2015/073688.
International Preliminary Report on Patentability with translation of Written Opinion dated Mar. 9, 2017, issued by the International Bureau in Application No. PCT/JP2015/073688.
International Search Report with Written Opinion dated Dec. 22, 2014, issued by the International Searching Authority in International Application No. PCT/JP2014/077368.
Serajuddin, "Salt formation to improve drug solubility", Advanced Drug Delivery Reviews, 2007, vol. 59, pp. 603-616.
Bastin et al., "Salt Selection and Optimisation Procedures for Pharmaceutical New Chemical Entities", Organic Process Research & Development, 2000, vol. 4, No. 5, pp. 427-435.
Liu, Rong, ed., "Water-Insoluble Drug Formation" (CRC Press, 2008) Chapter 15, pp. 417-435.
Morris et al., "An integrated approach to the selection of optimal salt form for a new drug candidate", International Journal of Pharmaceutics, 1994, vol. 105, pp. 209-217.
Adeyeye, Moji, ed., "Preformulation in Solid Dosage Form Development" (Informa Healthcare, 2008) Chapter 2.3, pp. 63-80.
Swarbrick et al., eds. "Encyclopedia of Pharmaceutical Technology 13", (Marcel Dekker, NY 1996), pp. 453-499.
Gould, "Salt selection for basic drugs", International Journal of Pharmaceutics, 1986, vol. 33, pp. 201-217.
International Preliminary Report on Patentability with translation of Written Opinion dated Apr. 28, 2016, issued by the International Bureau in International Application No. PCT/JP2014/077368.
Extended European Search Report dated Jul. 26, 2017, from the European Patent Office in European Application No. 15833175.1.
H. Quentmeier et al., "FLT3 mutations in acute myeloid leukemia cell lines", Leukemia, Nature Publishing Group, 2003, vol. 17, pp. 120-124 (5 pages total).
Office Action dated Aug. 29, 2017, from Japanese Patent Office in Japanese Application No. 2016-544276.
Yao et al., "FLT3 Expressing Leukemias Are Selectively Sensitive to Inhibitors of the Molecular Chaperone Heat Shock Protein 90 through Destabilization of Signal Transduction-Associated Kinases", Clinical Cancer Research, Oct. 1, 2003, vol. 9, No. 12, p. 4483-4493.
Issue Notification dated Sep. 9, 2015 from U.S. Appl. No. 14/516,337.
Corrected Notice of Allowance dated Sep. 8, 2015, which issued during the prosecution of U.S. Appl. No. 14/516,337.
Notice of Allowance dated May 8, 2015, which issued during the prosecution of U.S. Appl. No. 14/516,337.
Office Action dated Dec. 9, 2014 from U.S. Appl. No. 14/516,337.
Communication dated Aug. 26, 2015 from the European Patent Office in EP Application No. 13778349.4.
Communication dated Jul. 3, 2015 from the State Intellectual Property Office of the P.R.C. in Chinese Application No. 201380020639.X.
International Search Report dated Jun. 4, 2013 issued in PCT/JP2013/061273.
International Preliminary Report on Patentability with translation of Written Opinion dated Oct. 30, 2014 in International Application No. PCT/JP2013/061273.
Office Action dated Nov. 18, 2016 from U.S. Appl. No. 15/130,168.
Notice of Allowance dated Mar. 10, 2017, which issued during the prosecution of U.S. Appl. No. 15/130,168.
Corrected Notice of Allowability dated May 23, 2017, which issued during the prosecution of U.S. Appl. No. 15/130,168.
Issue Notification dated Jun. 21, 2017 from U.S. Appl. No. 15/130,168.
Communication dated Mar. 22, 2017 from the State Intellectual Property Office of the P.R.C. in Application No. 201480056478.4.
Communication dated Aug. 9, 2016 from the European Patent Office in Application No. 14854750.8.
Written Opinion dated Jun. 4, 2013 issued in PCT/JP2013/061273.
Office Action dated Dec. 29, 2017, from the Patent Office, Intellectual Property India in Indian Application No. 8285/CHENP/2014.
Office Action dated Sep. 8, 2017 from U.S. Appl. No. 15/436,037.
International Search Report for PCT/JP2016/070758, dated Oct. 11, 2016.
Written Opinion dated Oct. 11, 2016 issued in PCT/JP2016/070758.
International Preliminary Report on Patentability (PCT/IPEA/409) dated Mar. 22, 2017 issued in PCT/JP2016/070758.
Extended European Search Report dated Mar. 20, 2018 issued by the European Patent Office in counterpart European application No. 16824515.7.
Office Action dated May 22, 2018, from the Japanese Patent Office in counterpart Japanese Application No. 2015-141034.
Office Action dated Aug. 24, 2018 from the Russian Patent Office in counterpart Russian Application No. 2018100967/04.
Office Action dated Apr. 23, 2018 issued by the European Patent Office in European Patent Application No. 14854750.8.
Office Action dated May 28, 2019 issued in the corresponding Korean patent application No. 10-2018-7000990 with English Machine Translation.

METHOD FOR MANUFACTURING NITROGEN-CONTAINING HETEROCYCLIC COMPOUND AND INTERMEDIATE OF SAME

CROSS-REFERENCE TO RELATED APPLICATIONS

This application is a Divisional of U.S. application Ser. No. 15/867,122 filed Jan. 10, 2018, which is a Continuation of PCT International Application No. PCT/JP2016/070758 filed on Jul. 14, 2016, which claims priority under 35 U.S.C § 119(a) to Japanese Patent Application No. 2015-141034 filed on Jul. 15, 2015. Each of the above applications is hereby expressly incorporated by reference, in its entirety, into the present application.

BACKGROUND OF THE INVENTION

1. Field of the Invention

The present invention relates to a method for manufacturing a nitrogen-containing heterocyclic compound, which is useful as an Fms-like tyrosine kinase 3 inhibitor, and an intermediate of the nitrogen-containing heterocyclic compound.

2. Description of the Related Art

The Fms-like tyrosine kinase 3 (FLT3) is a protein belonging to the class III receptor tyrosine kinases, and has five immunoglobulin-like motifs in the extracellular domain at the N-terminal and two kinase domains at the C-terminal. FLT3 is expressed on normal CD34-positive human bone marrow progenitor cells and dendritic progenitor cells and plays an important role in growth, differentiation or the like of these cells. In addition, the ligand (FL) of FLT3 is one of the cytokines that is expressed in bone marrow stroma cells and T cells, affects the development of a number of hematopoietic lineage cells, and stimulates the growth of stem cells, progenitor cells, dendritic cells, and natural killer cells through interactions with other growth factors.

FLT3 dimerizes in a case where FL binds thereto, and then is activated by autophosphorylation. As a result, phosphorylation of AKT and ERK of PI3 and RAS signaling pathways is induced. FLT3 plays an important role in growth and differentiation of hematopoietic cells.

In normal bone marrow, the expression of FLT3 is limited to early progenitor cells, but in blood cancer, FLT3 is overexpressed or undergoes mutation, thereby contributing to malignant growth of cancer through the activation of the signaling pathways. Examples of the blood cancer include acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large cell lymphoma (ALCL), prolymphocytic leukemia (PML), juvenile myelomonocytic leukemia (JMML), adult T cell leukemia (ATL), myelodysplastic syndrome (MDS), and myeloproliferative disease (MPD).

For example, there is a report regarding a nitrogen-containing heterocyclic compound, which shows excellent FLT3 inhibitory activity and is useful as an active pharmaceutical ingredient of pharmaceutical products, and a method for manufacturing the compound (WO2013/157540A and WO2015/056683A).

SUMMARY OF THE INVENTION

There is a demand for a method for industrially manufacturing a nitrogen-containing heterocyclic compound which shows excellent FLT3 inhibitory activity and is useful as an active pharmaceutical ingredient of pharmaceutical products.

An object of the present invention is to provide a method for industrially manufacturing a nitrogen-containing heterocyclic compound, which shows excellent FLT3 inhibitory activity and is useful as an active pharmaceutical ingredient of pharmaceutical products, and an intermediate of the method.

Under the circumstances described above, the inventors of the present invention conducted an intensive study. As a result, the inventors obtained knowledge that a nitrogen-containing heterocyclic compound which shows excellent FLT3 inhibitory activity and is useful as an active pharmaceutical ingredient of pharmaceutical products can be industrially manufactured by the manufacturing method shown below. Furthermore, the inventors of the present invention obtained knowledge that a compound represented by General Formula [14] is a useful intermediate. Based on the knowledge, the inventors accomplished the present invention.

That is, the present invention provides the following.

<1> A method for manufacturing a compound represented by General Formula [5] or a salt thereof

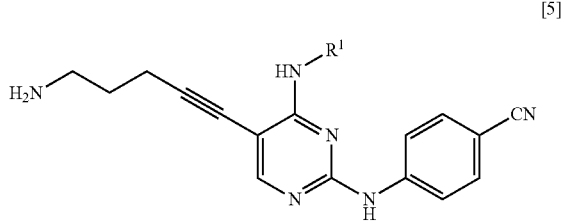

[5]

(in the formula, $R^1$ represents a $C_{1-6}$ alkyl group which may be substituted), the method comprising:

a step of reacting a compound represented by General Formula [1] or a salt thereof

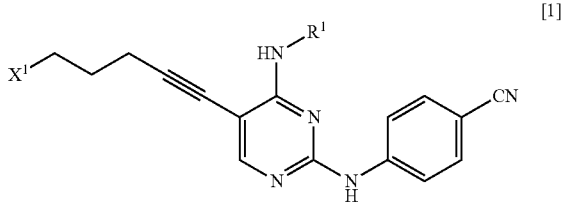

[1]

(in the formula, $R^1$ has the same definition as described above; and $X^1$ represents a leaving group) with a compound represented by General Formula [2] or a salt thereof

[2]

(in the formula, R² represents a hydrogen atom or an amino-protecting group; R³ represents a hydrogen atom or an amino-protecting group; and R² and R³ represent a phthaloyl group, which may be substituted, by being combined together), or with hexamethylenetetramine, thereby manufacturing a compound represented by General Formula [3] or a salt thereof

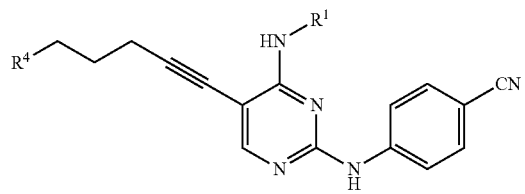

[3]

[in the formula, R⁴ represents a group represented by General Formula [4]

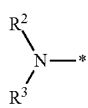

[4]

(in the formula, * represents a binding position; R² has the same definition as described above; R³ has the same definition as described above) or a hexamethylenetetraminium group; and R¹ has the same definition as described above], and then, if necessary, subjecting the obtained compound or a salt thereof to a deprotection reaction or a hydrolysis reaction.

<2> A method for manufacturing a compound represented by General Formula [5] or a salt thereof

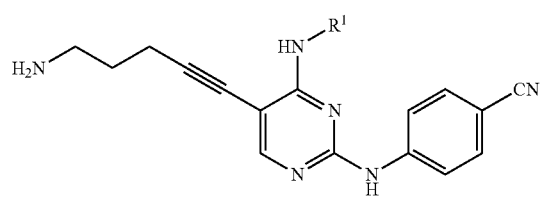

[5]

(in the formula, R¹ represents a $C_{1-6}$ alkyl group which may be substituted), the method comprising:

(1) step of reacting a compound represented by General Formula [6] or a salt thereof

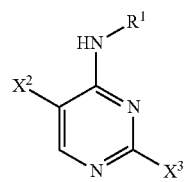

[6]

(in the formula, R¹ has the same definition as described above; X² has the same definition as described above; and X³ represents a leaving group) with 4-aminobenzonitrile or a salt thereof, thereby manufacturing a compound represented by General Formula [7] or a salt thereof

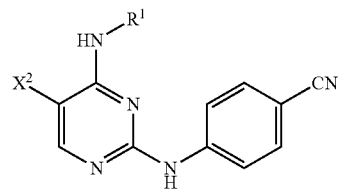

[7]

(in the formula, R¹ has the same definition as described above; and X² represents a leaving group);

(2) step of reacting the compound represented by General Formula [7] or a salt thereof with a compound represented by General Formula [8]

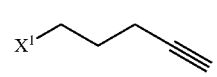

[8]

(in the formula, X¹ represents a leaving group), thereby manufacturing a compound represented by General Formula [1] or a salt thereof

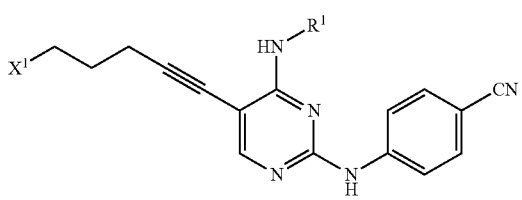

[1]

(in the formula, R¹ and X¹ have the same definition as described above); and (3) step of reacting the compound represented by General Formula [1] or a salt thereof with a compound represented by General Formula [2] or a salt thereof

[2]

(in the formula, R² represents a hydrogen atom or an amino-protecting group; R³ represents a hydrogen atom or an amino-protecting group; and R² and R³ represent a phthaloyl group, which may be substituted, by being combined together), or with hexamethylenetetramine, thereby manufacturing a compound represented by General Formula [3] or a salt thereof

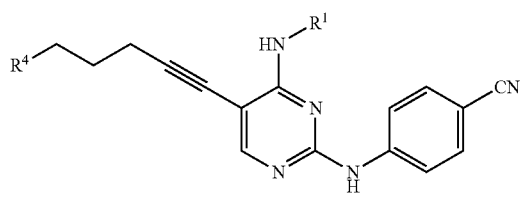

[3]

(in the formula, R⁴ represents a group represented by General Formula [4] or a hexamethylenetetraminium group; and R¹ has the same definition as described above)

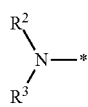

[4]

(in the formula, * represents a binding position; R² and R³ have the same definition as described above), and then, if necessary, subjecting the obtained compound or a salt thereof to a deprotection reaction or a hydrolysis reaction.

<3> The manufacturing method according to item <1> or <2> above,
wherein R¹ is a $C_{2-4}$ alkyl group.

<4> The manufacturing method according to any one of items <1> to <3> above,
wherein R² is a $C_{1-6}$ alkoxycarbonyl group, and
R³ is a $C_{1-6}$ alkoxycarbonyl group.

<5> The manufacturing method according to any one of items <2> to <4> above,
wherein X² is an iodine atom, and
X³ is a chlorine atom.

<6> A method for manufacturing a compound represented by General Formula [13] or a salt thereof

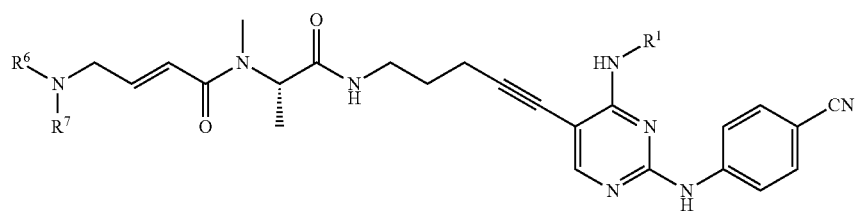

[13]

(in the formula, R¹ represents a $C_{1-6}$ alkyl group which may be substituted; R⁶ represents a hydrogen atom or a $C_{1-6}$ alkyl group which may be substituted; and R⁷ represents a $C_{1-6}$ alkyl group which may be substituted), the method comprising:

(1) step of reacting a compound represented by General Formula [1] or a salt thereof

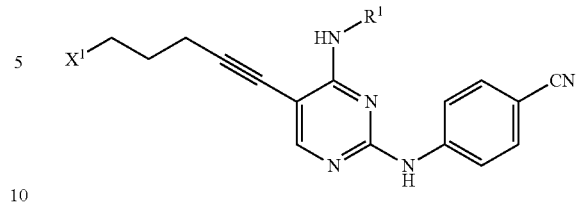

[1]

(in the formula, R¹ and has the same definition as described above; and X¹ represents a leaving group) with a compound represented by General Formula [2] or a salt thereof

[2]

(in the formula, R² represents a hydrogen atom or an amino-protecting group; R³ represents a hydrogen atom or an amino-protecting group; and R² and R³ represent a phthaloyl group, which may be substituted, by being combined together), or with hexamethylenetetramine, thereby manufacturing a compound represented by General Formula [3] or a salt thereof

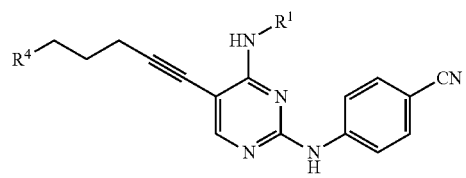

[3]

(in the formula, R⁴ represents a group represented by General Formula [4] or a hexamethylenetetraminium group; and R¹ has the same definition as described above)

[4]

(in the formula, * represents a binding position; R² and R³ have the same definition as described above; and R² and R³ represent a phthaloyl group, which may be substituted, by being combined together) and then, if necessary, subjecting the obtained compound or a salt thereof to a deprotection reaction or a hydrolysis reaction, to obtain a compound represented by General Formula [5] or a salt thereof

[5]

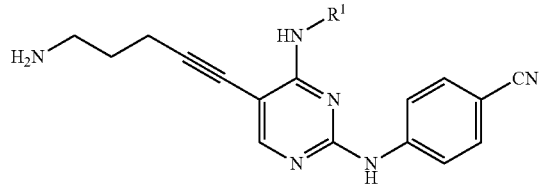

(in the formula, $R^1$ has the same definition as described above);

(2) step of reacting the compound represented by General Formula [5] or a salt thereof with a compound represented by General Formula [9] or a salt thereof

[9]

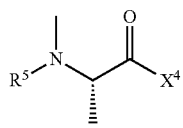

(in the formula, $R^5$ has the same definition as described above, and $X^4$ represents a hydroxyl group or a leaving group), thereby manufacturing a compound represented by General Formula [10] or a salt thereof

[10]

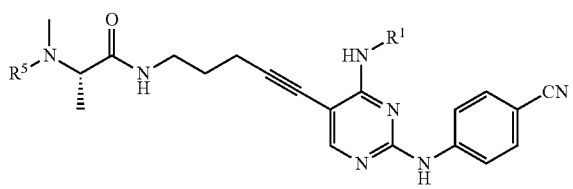

(in the formula, $R^1$ has the same definition as described above; and $R^5$ represents an amino-protecting group);

(3) step of subjecting the compound represented by General Formula [10] or a salt thereof to a deprotection, thereby manufacturing a compound represented by General Formula [11] or a salt thereof

[11]

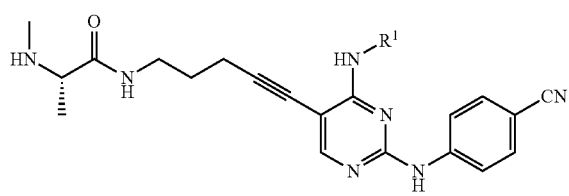

(in the formula, $R^1$ has the same definition as described above); and (4) step of reacting the compound represented by General Formula [11] or a salt thereof with a compound represented by General Formula [12] or a salt thereof

[12]

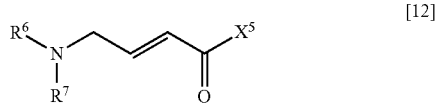

(in the formula, $R^6$ and $R^7$ have the same definition as described above; and $X^5$ represents a hydroxyl group or a leaving group).

<7> The manufacturing method according to item <6> above, wherein $R^1$ is a $C_{2-4}$ alkyl group.

<8> The manufacturing method according to item <6> or <7> above, wherein $R^2$ is a $C_{1-6}$ alkoxycarbonyl group, and $R^3$ is a $C_{1-6}$ alkoxycarbonyl group.

<9> The manufacturing method according to any one of items <6> to <8> above, wherein $R^6$ is a $C_{1-4}$ alkyl group, and $R^7$ is a $C_{1-4}$ alkyl group.

<10> A compound represented by General Formula [14] or a salt thereof

[14]

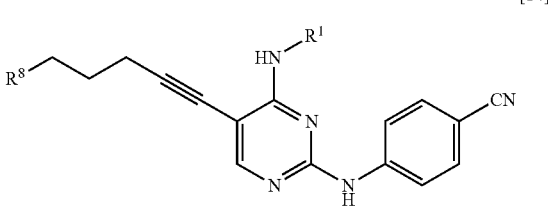

[in the formula, $R^1$ represents a $C_{1-6}$ alkyl group which may be substituted; and $R^8$ represents a leaving group, a group represented by General Formula [4a]

[4a]

(in the formula, $R^{2a}$ represents a $C_{1-6}$ alkoxycarbonyl group; $R^{3a}$ represents a $C_{1-6}$ alkoxycarbonyl group; and * represents a binding position), or a hexamethylenetetraminium group].

<11> The compound according to item <10> above or a salt thereof, wherein $R^1$ is a $C_{2-4}$ alkyl group, and $R^8$ is a leaving group.

<12> The compound according to item <10> above or a salt thereof,
wherein R¹ represents $C_{2-4}$ alkyl group; and R⁸ is a group represented by General Formula [4a]

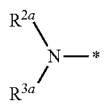

[4a]

(in the formula, $R^{2a}$ represents a $C_{1-6}$ alkoxycarbonyl group; $R^{3a}$ represents a $C_{1-6}$ alkoxycarbonyl group; and * represents a binding position).

<13> A $N^2$-(4-cyanophenyl)-5-iodo-$N^4$-propylpyrimidine-2,4-diamine hydrochloride.

The manufacturing method of the present invention is useful as a method for industrially manufacturing a nitrogen-containing heterocyclic compound which shows excellent FLT3 inhibitory activity and is useful as an active pharmaceutical ingredient of pharmaceutical products.

The compound of the present invention is useful as an intermediate used in the method for industrially manufacturing a nitrogen-containing heterocyclic compound which shows excellent FLT3 inhibitory activity and is useful as an active pharmaceutical ingredient of pharmaceutical products.

DESCRIPTION OF THE PREFERRED EMBODIMENTS

Hereinafter, the present invention will be specifically described.

In the present invention, unless otherwise specified, % means % by mass.

In the present invention, unless otherwise specified, each term has the following meaning.

The halogen atom means a chlorine atom, a bromine atom, or an iodine atom.

The $C_{1-6}$ alkyl group means a linear or branched $C_{1-6}$ alkyl group such as a methyl, ethyl, propyl, isopropyl, butyl, sec-butyl, isobutyl, tert-butyl, pentyl, isopentyl, 2-methylbutyl, 2-pentyl, 3-pentyl, or hexyl group.

The $C_{1-4}$ alkyl group means a methyl, ethyl, propyl, isopropyl, butyl, sec-butyl, isobutyl, or tert-butyl group.

The $C_{2-4}$ alkyl group means an ethyl, propyl, isopropyl, butyl, sec-butyl, isobutyl, or tert-butyl group.

The aryl group means a phenyl or naphthyl group.

The ar-$C_{1-6}$ alkyl group means an ar-$C_{1-6}$ alkyl group such as a benzyl, diphenylmethyl, trityl, phenethyl, 2-phenylpropyl, 3-phenylpropyl, or naphthylmethyl group.

The $C_{1-6}$ alkoxy group means a linear or branched $C_{1-6}$ alkoxy group such as a methoxy, ethoxy, propoxy, isopropoxy, butoxy, isobutoxy, sec-butoxy, tert-butoxy, pentyloxy, or hexyloxy group.

The $C_{1-6}$ alkoxy $C_{1-6}$ alkyl group means a $C_{1-6}$ alkyloxy $C_{1-6}$ alkyl group such as a methoxymethyl or 1-ethoxyethyl group.

The $C_{2-6}$ alkanoyl group means a linear or branched $C_{2-6}$ alkanoyl group such as an acetyl, propionyl, valeryl, isovaleryl, or pivaloyl group.

The aroyl group means a benzoyl or naphthoyl group.

The heterocyclic carbonyl group means a furoyl, thenoyl, pyrrolidinylcarbonyl, piperidinylcarbonyl, piperazinylcarbonyl, morpholinylcarbonyl, or pyridinylcarbonyl group.

The acyl group means a formyl group, a $C_{2-6}$ alkanoyl group, an aroyl group, or a heterocyclic carbonyl group.

The $C_{1-6}$ alkoxycarbonyl group means a linear or branched $C_{1-6}$ alkyloxycarbonyl group such as a methoxycarbonyl, ethoxycarbonyl, propoxycarbonyl, isopropoxycarbonyl, tert-butoxycarbonyl, or 1,1-dimethylpropoxycarbonyl group.

The $C_{3-6}$ alkoxycarbonyl group means a linear or branched $C_{3-6}$ alkyloxycarbonyl group such as a propoxycarbonyl, isopropoxycarbonyl, tert-butoxycarbonyl, or 1,1-dimethylpropoxycarbonyl group.

The ar-$C_{1-6}$ alkoxycarbonyl group means an ar-$C_{1-6}$ alkyloxycarbonyl group such as a benzyloxycarbonyl or phenethyloxycarbonyl group.

The aryloxycarbonyl group means a phenyloxycarbonyl or naphthyloxycarbonyl group.

The $C_{1-6}$ alkylamino group means a linear or branched $C_{1-6}$ alkylamino group such as a methylamino, ethylamino, propylamino, isopropylamino, butylamino, sec-butylamino, tert-butylamino, pentylamino, or hexylamino group.

The di($C_{1-6}$ alkyl)amino group means a linear or branched di($C_{1-6}$ alkyl)amino group such as a dimethylamino, diethylamino, dipropylamino, diisopropylamino, dibutylamino, di(tert-butyl)amino, dipentylamino, dihexylamino, (ethyl)(methyl)amino, or (methyl)(propyl)amino group.

The $C_{1-6}$ alkylsulfonyl group means a $C_{1-6}$ alkylsulfonyl group such as a methylsulfonyl, ethylsulfonyl, or propylsulfonyl group.

The arylsulfonyl group means a benzenesulfonyl, p-toluenesulfonyl, or naphthalenesulfonyl group.

The $C_{1-6}$ alkylsulfonyloxy group means a $C_{1-6}$ alkylsulfonyloxy group such as a methylsulfonyloxy or ethylsulfonyloxy group.

The arylsulfonyloxy group means a benzenesulfonyloxy or p-toluenesulfonyloxy group.

The silyl group means a trimethylsilyl, triethylsilyl, or tributylsilyl group.

The leaving group means a halogen atom, a $C_{1-6}$ alkylsulfonyloxy group, or an arylsulfonyloxy group. The $C_{1-6}$ alkylsulfonyloxy group and the arylsulfonyloxy group may be substituted with one or more groups selected from the substituent group A.

The substituent group A and the substituent group B each mean the following group.

Substituent group A: a fluorine atom, a halogen atom, a cyano group, an amino group which may be protected, a hydroxyl group which may be protected, a $C_{1-6}$ alkyl group, an aryl group, a $C_{1-6}$ alkoxy group, a $C_{1-6}$ alkylamino group, a di($C_{1-6}$ alkyl)amino group, and an oxo group.

Substituent group B: a fluorine atom, a halogen atom, a $C_{1-6}$ alkyl group, and a $C_{1-6}$ alkoxy group.

The amino-protecting group includes all the groups which can be used as general protecting groups for an amino group, and examples thereof include the groups described in, for example, Greene's Protective Groups in Organic Synthesis, 5$^{th}$ edition, pp. 895~1193, 2014, John Wiley & Sons, INC. Specifically, examples of the amino-protecting group include an ar-$C_{1-6}$ alkyl group, a $C_{1-6}$ alkoxy $C_{1-6}$ alkyl group, an acyl group, a $C_{1-6}$ alkoxycarbonyl group, an ar-$C_{1-6}$ alkoxycarbonyl group, an aryloxycarbonyl group, a $C_{1-6}$ alkylsulfonyl group, an arylsulfonyl group, and a silyl group. These groups may be substituted with one or more groups selected from the substituent group A.

The hydroxyl-protecting group includes all the groups that can be used as general protecting groups for a hydroxyl group, and examples thereof include the groups described in Greene's Protective Groups in Organic Synthesis, 5$^{th}$ edition, pp. 17~471, 2014, John Wiley & Sons, INC. Specifically, examples of the hydroxyl-protecting group include a $C_{1-6}$ alkyl group, an ar-$C_{1-6}$ alkyl group, a $C_{1-6}$ alkoxy $C_{1-6}$ alkyl group, an acyl group, a $C_{1-6}$ alkoxycarbonyl group, an ar-$C_{1-6}$ alkoxycarbonyl group, a $C_{1-6}$ alkylsulfonyl group, an arylsulfonyl group, a silyl group, a tetrahydrofuranyl group, and a tetrahydropyranyl group.

These groups may be substituted with one or more groups selected from the substituent group A.

Aliphatic hydrocarbons mean pentane, hexane, heptane, cyclohexane, methylcyclohexane, or ethylcyclohexane.

Halogenated hydrocarbons mean dichloromethane, chloroform, or dichloroethane.

Ethers mean diethylether, diisopropylether, tetrahydrofuran, 2-methyltetrahydrofuran, 1,4-dioxane, anisole, ethylene glycol dimethyl ether, diethylene glycol dimethyl ether, or diethylene glycol diethyl ether.

Alcohols mean methanol, ethanol, propanol, 2-propanol, butanol, 2-methyl-2-propanol, ethylene glycol, propylene glycol, or diethylene glycol.

Ketones mean acetone, 2-butanone, or 4-methyl-2-pentanone.

Esters mean methyl acetate, ethyl acetate, propyl acetate, isopropyl acetate, or butyl acetate.

Amides mean N,N-dimethylformamide, N,N-dimethylacetamide, or N-methylpyrrolidone.

Nitriles mean acetonitrile or propionitrile.

Sulfoxides mean dimethylsulfoxide or sulfolane.

Aromatic hydrocarbons mean benzene, toluene, or xylene.

The inorganic base means sodium hydroxide, potassium hydroxide, sodium methoxide, sodium tert-butoxide, potassium tert-butoxide, sodium hydrogen carbonate, sodium carbonate, potassium carbonate, tripotassium phosphate, potassium acetate, cesium fluoride, or cesium carbonate.

The organic base means triethylamine, N,N-diisopropylethylamine, 1,8-diazabicyclo(5.4.0)undec-7-ene (DBU), pyridine, 4-dimethylaminopyridine, or N-methylmorpholine.

Examples of salts of the compounds represented by General Formulae [1], [2], [3], [5], [6], [7], [9], [10], [11], [12], [13], and [14] include salts in generally known basic groups such as an amino group and salts in acidic groups such as a hydroxyl group and a carboxyl group.

Examples of the salts in basic groups include salts with mineral acids such as hydrochloric acid, hydrobromic acid, nitric acid, and sulfuric acid; salts with organic carboxylic acids such as formic acid, acetic acid, citric acid, oxalic acid, fumaric acid, maleic acid, succinic acid, malic acid, tartaric acid, aspartic acid, trichloroacetic acid, and trifluoroacetic acid; and salts with sulfonic acids such as methanesulfonic acid, benzenesulfonic acid, p-toluenesulfonic acid, mesitylene sulfonic acid, and naphthalene sulfonic acid.

Examples of the salts in acidic groups include salts with alkali metals such as sodium and potassium; salts with alkaline earth metals such as calcium and magnesium; ammonium salts; and salts with nitrogen-containing organic bases such as trimethylamine, triethylamine, tributylamine, pyridine, N,N-dimethylaniline, N-methylpiperidine, N-methylmorpholine, diethylamine, dicyclohexylamine, procaine, dibenzylamine, N-benzyl-β-phenethylamine, 1-ephenamine and N,N'-dibenzylethylenediamine.

Among the aforementioned salts, pharmacologically acceptable salts are preferred salts.

$R^1$ is a $C_{1-6}$ alkyl group which may be substituted.

The $C_{1-6}$ alkyl group represented by $R^1$ may be substituted with one or more groups selected from the substituent group A.

$R^1$ is preferably a $C_{1-6}$ alkyl group, more preferably a $C_{2-4}$ alkyl group, and even more preferably a propyl group.

$R^2$ is a hydrogen atom or an amino-protecting group.

$R^2$ is preferably an amino-protecting group, more preferably a $C_{1-6}$ alkoxycarbonyl group, even more preferably a $C_{3-6}$ alkoxycarbonyl group, and particularly preferably a tert-butoxycarbonyl group.

$R^3$ is a hydrogen atom or an amino-protecting group.

$R^3$ is preferably an amino-protecting group, more preferably a $C_{1-6}$ alkoxycarbonyl group, even more preferably a $C_{3-6}$ alkoxycarbonyl group, and particularly preferably a tert-butoxycarbonyl group.

$R^2$ and $R^3$ may form a phthaloyl group, which may be substituted, by being combined together The phthaloyl group formed by $R^2$ and $R^3$ combined together may be substituted with one or more groups selected from the substituent group A.

It is preferable that $R^2$ and $R^3$ form a phthaloyl group by being combined to each other.

$R^{2a}$ is a $C_{1-6}$ alkoxycarbonyl group.

$R^{2a}$ is preferably a $C_{3-6}$ alkoxycarbonyl group, and more preferably a tert-butoxycarbonyl group.

$R^{3a}$ is a $C_{1-6}$ alkoxycarbonyl group.

$R^{3a}$ is preferably a $C_{3-6}$ alkoxycarbonyl group, and more preferably a tert-butoxycarbonyl group.

$R^4$ is a group represented by General Formula [4] or a hexamethylenetetraminium group.

[4]

(In the formula, $R^2$, $R^3$, and * have the same definition as described above).

$R^4$ is preferably a group represented by General Formula [4].

The groups preferred as $R^2$ are the same as described above.

The groups preferred as $R^3$ are the same as described above.

$R^5$ is an amino-protecting group.

$R^5$ is preferably a $C_{1-6}$ alkoxycarbonyl group, and more preferably a tert-butoxycarbonyl group.

$R^6$ is a hydrogen atom or a $C_{1-6}$ alkyl group which may be substituted.

The $C_{1-6}$ alkyl group represented by $R^6$ may be substituted with one or more groups selected from the substituent group A.

$R^6$ is preferably a $C_{1-6}$ alkyl group, more preferably a $C_{1-4}$ alkyl group, and even more preferably a methyl group.

$R^7$ is a $C_{1-4}$ alkyl group which may be substituted.

The $C_{1-6}$ alkyl group represented by $R^7$ may be substituted with one or more groups selected from the substituent group A.

$R^7$ is preferably a $C_{1-6}$ alkyl group, more preferably a $C_{1-4}$ alkyl group, and even more preferably a methyl group.

$R^8$ is a leaving group, a group represented by General Formula [4a], or a hexamethylenetetraminium group.

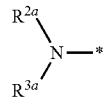

[4a]

(In the formula, $R^{2a}$, $R^{3a}$, and * have the same definition as described above.)

$R^8$ is preferably a leaving group or a group represented by General Formula [4a].

In a case where $R^8$ is a leaving group, $R^8$ is preferably a halogen atom and more preferably a chlorine atom.

In a case where $R^8$ is a group represented by General Formula [4a], $R^8$ is preferably a group represented by General Formula [4a] in which $R^{2a}$ is a $C_{3-6}$ alkoxycarbonyl group and $R^{3a}$ is a $C_{3-6}$ alkoxycarbonyl group, and more preferably a di(tert-butoxycarbonyl)amino group.

The groups preferred as $R^{2a}$ are the same as described above.

The groups preferred as $R^{3a}$ are the same as described above.

$X^1$ is a leaving group.

$X^1$ is preferably a halogen atom, a $C_{1-6}$ alkylsulfonyloxy group which may be substituted with one or more groups selected from the substituent group B or an arylsulfonyloxy group which may be substituted with one or more groups selected from the substituent group B, more preferably a halogen atom, and even more preferably a chlorine atom.

$X^2$ is a leaving group.

$X^2$ is preferably a halogen atom, and more preferably an iodine atom.

$X^3$ is a leaving group.

$X^3$ is preferably a halogen atom, and more preferably a chlorine atom.

$X^4$ is a hydroxyl group or a leaving group.

$X^4$ is preferably a hydroxyl group.

In a case where $X^4$ is a leaving group, $X^4$ is preferably a halogen atom and more preferably a chlorine atom.

$X^5$ is a hydroxyl group or a leaving group.

$X^5$ is preferably a hydroxyl group.

In a case where $X^5$ is a leaving group, $X^5$ is preferably a halogen atom and more preferably a chlorine atom.

In a case where the compound represented by General Formula [14] or a salt thereof includes an isomer (for example, an optical isomer, a geometric isomer, a tautomer, or the like), the present invention includes the isomer, an anhydride, a solvate, a hydrate, and crystals of various shapes.

Next, the compound of the present invention will be described.

The compound of the present invention is a compound represented by General Formula [14] or a salt thereof.

[14]

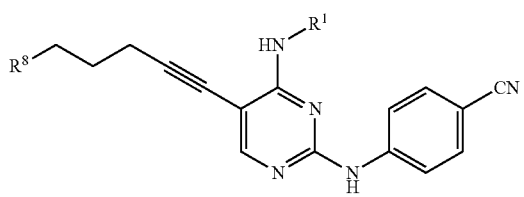

(In the formula, $R^1$ and $R^8$ have the same definition as described above.)

The groups preferred as $R^1$ are the same as described above.

The groups preferred as $R^8$ are the same as described above.

Next, the manufacturing method of the present invention will be described.

[Manufacturing Method A]

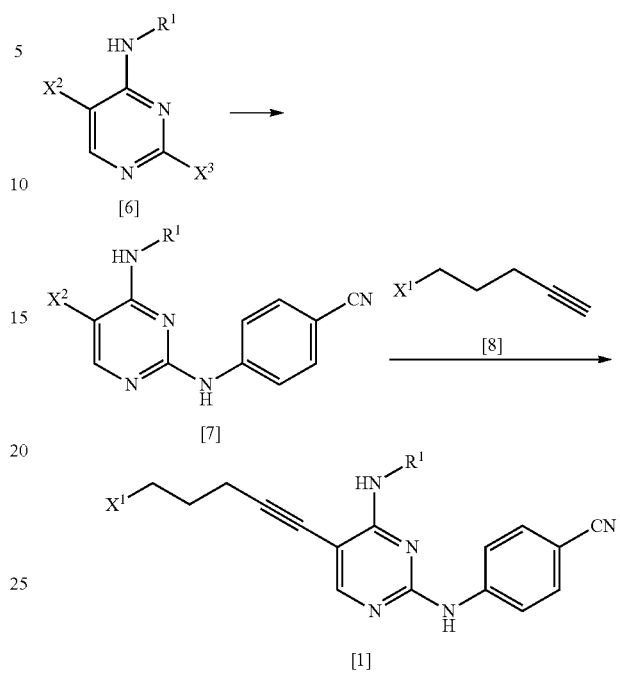

(In the formula, $R^1$, $X^1$, $X^2$, and $X^3$ have the same definition as described above.)

<First Step>

As the compound represented by General Formula [6], for example, 2-chloro-5-iodo-N-propylpyrimidin-4-amine or the like is known.

The compound represented by General Formula [7] or a salt thereof can be manufactured by reacting the compound represented by General Formula [6] or a salt thereof with 4-aminobenzonitrile or a salt thereof in the presence of an acid.

The solvent used in this reaction is not particularly limited as long as the solvent does not affect the reaction. Examples of the solvent include aliphatic hydrocarbons, halogenated hydrocarbons, ethers, esters, amides, nitriles, sulfoxides, and aromatic hydrocarbons. These solvents may be used by being mixed together.

Examples of preferred solvents include amides. Among these, N,N-dimethylformamide, N,N-dimethylacetamide, and N-methylpyrrolidone are preferable, and N-methylpyrrolidone is more preferable.

The amount of the solvent used is not particularly limited, and may be 1 to 500 times (v/w) the amount of the compound represented by General Formula [6] or a salt thereof.

Examples of the acid used in this reaction include mineral acids such as hydrochloric acid, hydrobromic acid, nitric acid, and sulfuric acid; and sulfonic acids such as methanesulfonic acid, benzenesulfonic acid, p-toluenesulfonic acid, mesitylene sulfonic acid, naphthalene sulfonic acid, and camphorsulfonic acid. Among these, hydrochloric acid and camphorsulfonic acid are preferable, and hydrochloric acid is more preferable.

The amount of the acid used may be 0.5 to 5 times the amount of the compound represented by General Formula [6] or a salt thereof in terms of mole.

The amount of 4-aminobenzonitrile used may be 1 to 50 times and preferably 1 to 5 times the amount of the compound represented by General Formula [6] or a salt thereof in terms of mole.

This reaction may be performed for 30 minutes to 48 hours at a temperature of −30° C. to 150° C. and preferably at a temperature of 0° C. to 100° C.

The compound represented by General Formula [7] is preferably isolated as a salt. Examples of preferred salts include hydrochloride. In a case where the compound is isolated as hydrochloride, the compound represented by General Formula [7] having high purity can be obtained by a simple operation with high yield.

<Second Step>

As the compound represented by General Formula [8], for example, 5-chloro-1-pentyne or the like is known.

The compound represented by General Formula [1] or a salt thereof can be manufactured by reacting the compound represented by General Formula [7] or a salt thereof with the compound represented by General Formula [8] in the presence of a palladium catalyst, a copper salt, and a base.

The solvent used in this reaction is not particularly limited as long as the solvent does not affect the reaction. Examples of the solvent include aliphatic hydrocarbons, halogenated hydrocarbons, ethers, esters, amides, nitriles, sulfoxides, and aromatic hydrocarbons. These solvents may be used by being mixed together.

Examples of preferred solvents include ethers and amides. Among these, tetrahydrofuran and N,N-dimethylformamide are more preferable, and tetrahydrofuran is even more preferable.

The amount of the solvent used is not particularly limited, and may be 1 to 500 times (v/w) the amount of the compound represented by General Formula [7] or a salt thereof.

The amount of the compound represented by General Formula [8] used may be 1 to 50 times and preferably 1 to 5 times the amount of the compound represented by General Formula [7] or a salt thereof in terms of mole.

Examples of the palladium catalyst used in this reaction include metal palladium such as palladium-carbon and palladium black; an inorganic palladium salt such as palladium chloride; an organic palladium salt such as palladium acetate; chloro(2-(dicyclohexylphosphino)-3,6-dimethoxy-2',4',6'-triisopropyl-1,1'-biphenyl)(2-(2-aminoethyl)phenyl)palladium(II); an organic palladium complex such as tetrakis(triphenylphosphine)palladium(0), bis(triphenylphosphine)palladium(II) dichloride, bis(di-tert-butyl(4-dimethylaminophenyl)phosphine)dichloropalladium(II), 1,1'-bis(diphenylphosphino)ferrocene palladium(II) dichloride, (E)-di(μ-acetate)bis(ortho-(di-ortho-tolylphosphino)benzyl)dipalladium(II), and tris(dibenzylideneacetone)dipalladium(0); a polymer-supported organic palladium complex such as polymer-supported bis(acetate)triphenylphosphine palladium(II) and polymer-supported di(acetate)dicyclohexylphenylphosphine palladium(II); and the like. Among these, an organic palladium complex is preferable.

The amount of the palladium catalyst used may be 0.0001 to 2 times and preferably 0.001 to 0.2 times the amount of the compound represented by General Formula [7] or a salt thereof in terms of mole.

Examples of the copper salt used in this reaction include copper(I) chloride, copper(I) bromide, copper(I) iodide, and copper(II) acetate. Among these, copper(I) iodide is preferable.

The amount of the copper salt used may be 0.0001 to 2 times and preferably 0.001 to 0.5 times the amount of the compound represented by General Formula [7] or a salt thereof in terms of mole.

Examples of the base used in this reaction include organic bases. Among these, triethylamine and N,N-diisopropylethylamine are preferable, and triethylamine is more preferable.

The amount of the base used may be 0.1 to 50 times and preferably 1 to 10 times the amount of the compound represented by General Formula [7] or a salt thereof.

This reaction may be performed for 30 minutes to 48 hours at a temperature of −30° C. to 150° C. and preferably at a temperature of 0° C. to 100° C.

As this step, a manufacturing method using 5-chloro-1-pentyne is preferable.

By the manufacturing method using 5-chloro-1-pentyne, the compound represented by General Formula [1] or a salt thereof having high purity can be manufactured by a simple operation with high yield.

The compound represented by General Formula [1] or a salt thereof is a stable compound, and it is easy to handle the compound.

As the method for manufacturing the compound represented by General Formula [1] or a salt thereof from the compound represented by General Formula [7] or a salt thereof, the following method can be used.

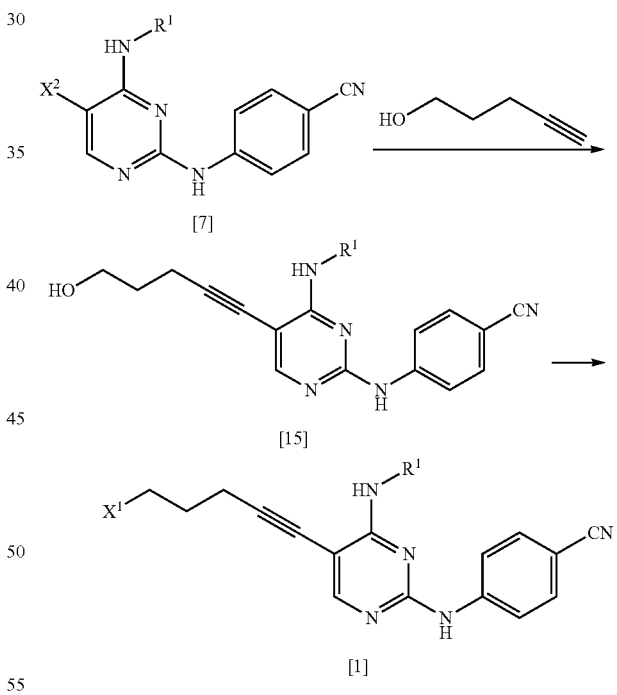

(In the formula, $R^1$, $X^1$, and $X^2$ have the same definition as described above.)

The compound represented by General Formula [15] or a salt thereof can be manufactured by reacting the compound represented by General Formula [7] or a salt thereof with 4-pentyn-1-ol in the presence of a palladium catalyst, a copper salt, and a base.

This reaction may be performed based on <Second step> of Manufacturing method A.

The compound represented by General Formula [1] or a salt thereof can be manufactured by reacting the compound represented by General Formula [15] or a salt thereof with sulfonyl halide in the presence of a base.

The solvent used in this reaction is not particularly limited as long as the solvent does not affect the reaction. Examples of the solvent include aliphatic hydrocarbons, halogenated hydrocarbons, ethers, esters, amides, nitriles, sulfoxides, and aromatic hydrocarbons. These solvents may be used by being mixed together.

Examples of preferred solvents include halogenated hydrocarbons, ethers, and amides. Among these, halogenated hydrocarbons are more preferable.

The amount of the solvent used is not particularly limited, and may be 1 to 500 times (v/w) the amount of the compound represented by General Formula [15] or a salt thereof.

Examples of the sulfonyl halide used in this reaction include methanesulfonyl chloride, trifluoromethanesulfonyl chloride, benzenesulfonyl chloride, and p-toluenesulfonyl chloride.

Examples of preferred sulfonyl halide include methanesulfonyl chloride and p-toluenesulfonyl chloride.

The amount of the sulfonyl halide used may be 1 to 10 times and preferably 1 to 5 times the amount of the compound represented by General Formula [15] or a salt thereof in terms of mole.

Examples of the base used in this reaction include organic bases. Among these, triethylamine and N,N-diisopropylethylamine are preferable.

The amount of the base used may be 1 to 10 times and preferably 1 to 5 times the amount of the compound represented by General Formula [15] or a salt thereof in terms of mole.

This reaction may be performed for 30 minutes to 48 hours at a temperature of −30° C. to 150° C. and preferably at a temperature of 0° C. to 100° C.

[Manufacturing Method B]

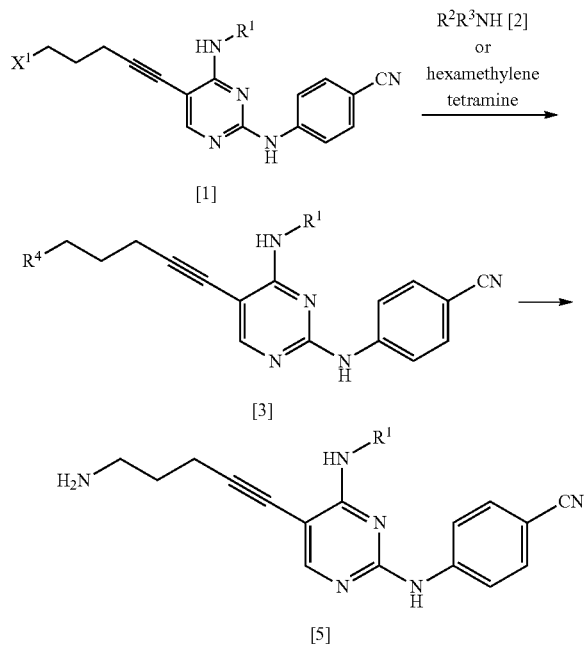

(In the formula, $R^1$, $R^2$, $R^3$, $R^4$, and $X^1$ have the same definition as described above.)

The compound represented by General Formula [5] or a salt thereof can be manufactured by reacting the compound represented by General Formula [1] or a salt thereof with the compound represented by General Formula [2] or a salt thereof or with hexamethylenetetramine and then, if necessary, subjecting the obtained compound or a salt thereof to a deprotection reaction or a hydrolysis reaction.

(1a) Manufacturing Method Using Ammonia [2a]

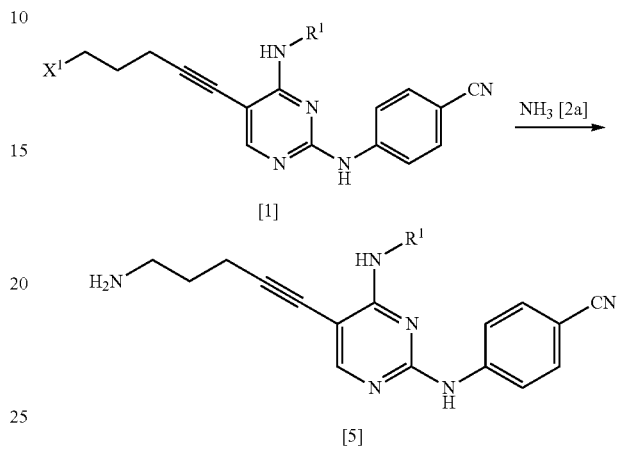

(In the formula, $R^1$ and $X^1$ have the same definition as described above.)

The compound represented by General Formula [5] or a salt thereof can be manufactured by reacting the compound represented by General Formula [1] or a salt thereof with ammonia [2a] or a salt thereof in the presence or absence of a base.

The solvent used in this reaction is not particularly limited as long as the solvent does not affect the reaction. Examples of the solvent include aliphatic hydrocarbons, halogenated hydrocarbons, ethers, alcohols, amides, nitriles, sulfoxides, and aromatic hydrocarbons. These solvents may be used by being mixed together.

Examples of preferred solvents include amides. Among these, N,N-dimethylacetamide is more preferable.

The amount of the solvent used is not particularly limited, and may be 1 to 50 times (v/w) the amount of the compound represented by General Formula [1] or a salt thereof.

Examples of the salt of ammonia include ammonium chloride, ammonium bromide, ammonium iodide, and ammonium carbonate. Among these, ammonium iodide is preferable.

The amount of ammonia or a salt thereof used may be 1 to 50 times and preferably 1 to 10 times the amount of the compound represented by General Formula [1] in terms of mole.

Examples of the base used as desired in this reaction include organic bases. Among these, triethylamine and N,N-diisopropylethylamine are preferable.

The amount of the base used may be 1 to 50 times and preferably 1 to 10 times the amount of the compound represented by General Formula [1] in terms of mole.

In this reaction, a salt may be added. Examples of the salt include potassium iodide and the like.

The amount of the salt used may be 0.1 to 50 times and preferably 0.1 to 10 times the amount of the compound represented by General Formula [1] in terms of mole.

This reaction may be performed for 30 minutes to 48 hours at a temperature of −30° C. to 150° C. and preferably at a temperature of 0° C. to 100° C.

(1b) Manufacturing Method Using Compound Represented by General Formula [2b] or Salt Thereof

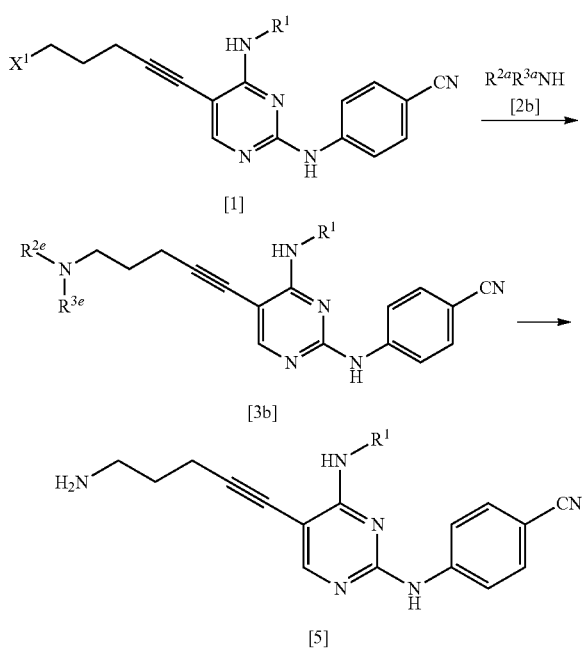

(In the formula, $R^1$, $R^{2a}$, $R^{3a}$, and $X^1$ have the same definition as described above.)

As the compound represented by General Formula [2b], for example, di(tert-butoxycarbonyl)amine or the like is known.

The compound represented by General Formula [3b] or a salt thereof can be manufactured by reacting the compound represented by General Formula [1] or a salt thereof with the compound represented by General Formula [2b] or a salt thereof in the presence of a base.

The solvent used in this reaction is not particularly limited as long as the solvent does not affect the reaction. Examples of the solvent include aliphatic hydrocarbons, halogenated hydrocarbons, ethers, esters, amides, nitriles, sulfoxides, and aromatic hydrocarbons. These solvents may be used by being mixed together.

Examples of preferred solvents include amides. Among these, N-methylpyrrolidone is more preferable.

The amount of the solvent used is not particularly limited, and may be 1 to 50 times (v/w) the amount of the compound represented by General Formula [1] or a salt thereof.

The amount of the compound represented by General Formula [2b] or a salt thereof used may be 1 to 10 times and preferably 1 to 5 times the amount of the compound represented by General Formula [1] or a salt thereof in terms of mole.

Examples of the base used in this reaction include organic bases and inorganic bases. Among these, inorganic bases are preferable, and potassium carbonate is more preferable.

The amount of the base used may be 1 to 50 times and preferably 1 to 10 times the amount of the compound represented by General Formula [1] in terms of mole.

In this reaction, a salt may be added. Examples of the salt include potassium iodide and the like.

The amount of the salt used may be 0.1 to 50 times and preferably 0.1 to 10 times the amount of the compound represented by General Formula [1] in terms of mole.

This reaction may be performed for 30 minutes to 48 hours at a temperature of −30° C. to 150° C. and preferably at a temperature of 0° C. to 100° C.

The compound represented by General Formula [5] or a salt thereof can be manufactured by subjecting the compound represented by General Formula [3b] or a salt thereof to a deprotection reaction or a hydrolysis reaction.

This reaction can be performed by the method described in, for example, Greene's Protective Groups in Organic Synthesis, 5th edition, pp. 895~1193, 2014, John Wiley & Sons, INC.

(1c) Manufacturing Method Using Potassium Phthalimide [2c]

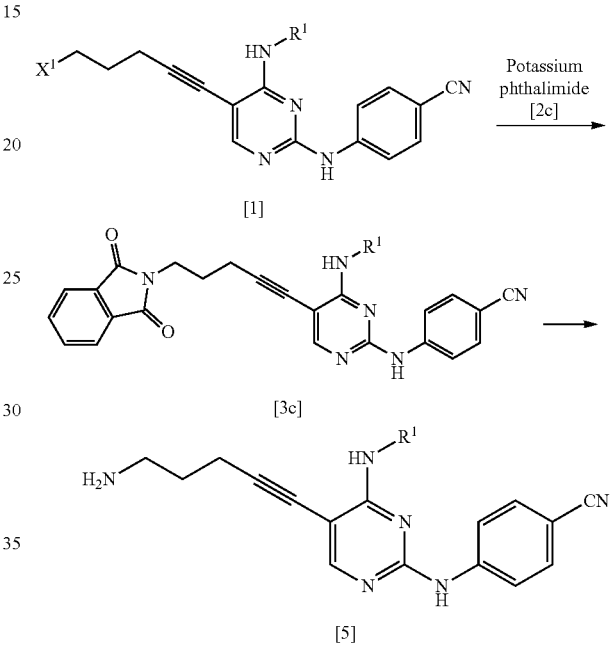

(In the formula, $R^1$ and $X^1$ have the same definition as described above.)

The compound represented by General Formula [3c] or a salt thereof can be manufactured by reacting the compound represented by General Formula [1] or a salt thereof with potassium phthalimide [2c].

The solvent used in this reaction is not particularly limited as long as the solvent does not affect the reaction. Examples of the solvent include aliphatic hydrocarbons, halogenated hydrocarbons, ethers, esters, amides, nitriles, sulfoxides, and aromatic hydrocarbons. These solvents may be used by being mixed together.

Examples of preferred solvents include sulfoxides. Among these, dimethylsulfoxide is more preferable.

The amount of the solvent used is not particularly limited, and may be 1 to 50 times (v/w) the amount of the compound represented by General Formula [1] or a salt thereof.

The amount of the potassium phthalimide used may be 1 to 10 times and preferably 1 to 5 times the amount of the compound represented by General Formula [1] or a salt thereof in terms of mole.

The potassium phthalimide may be prepared in the system by using phthalimide and potassium carbonate, for example.

It is preferable that a salt is added in this reaction. Examples of the salt include sodium iodide, potassium iodide, and lithium iodide. Among these, lithium iodide is preferable.

The amount of the salt used may be 0.1 to 50 times and preferably 0.1 to 10 times the amount of the compound represented by General Formula [1] in terms of mole.

This reaction may be performed for 30 minutes to 48 hours at a temperature of −30° C. to 150° C. and preferably at a temperature of 0° C. to 100° C.

The compound represented by General Formula [5] or a salt thereof can be manufactured by subjecting the compound represented by General Formula [3c] or a salt thereof to a deprotection reaction.

This reaction can be performed by the method described in, for example, Greene's Protective Groups in Organic Synthesis, 5th edition, pp. 895~1193, 2014, John Wiley & Sons, INC.

Specifically, for example, a method using hydrazine or ethylenediamine may be used, and a method using ethylenediamine is preferable.

(1d) Manufacturing Method Using Hexamethylenetetramine

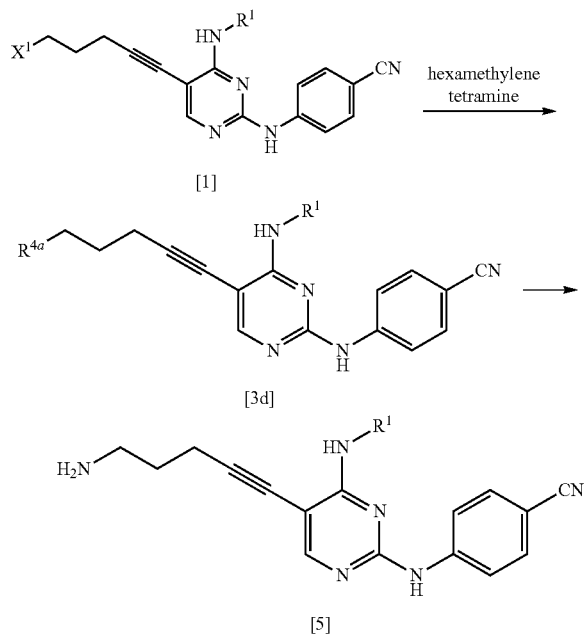

(In the formula, $R^{4a}$ represents a hexamethylenetetraminium group; and $R^1$ and $X^1$ have the same definition as described above.)

The compound represented by General Formula [3d] or a salt thereof can be manufactured by reacting the compound represented by General Formula [1] or a salt thereof with hexamethylenetetramine.

The solvent used in this reaction is not particularly limited as long as the solvent does not affect the reaction. Examples of the solvent include aliphatic hydrocarbons, halogenated hydrocarbons, ethers, esters, amides, nitriles, sulfoxides, and aromatic hydrocarbons. These solvents may be used by being mixed together.

Examples of preferred solvents include amides.

The amount of the solvent used is not particularly limited, and may be 1 to 50 times (v/w) the amount of the compound represented by General Formula [1].

The amount of the hexamethylenetetramine used may be 1 to 10 times and preferably 1 to 5 times the amount of the compound represented by General Formula [1] in terms of mole.

This reaction may be performed for 30 minutes to 48 hours at a temperature of −30° C. to 150° C. and preferably at a temperature of 0° C. to 100° C.

The compound represented by General Formula [5] or a salt thereof can be manufactured by subjecting the compound represented by General Formula [3d] or a salt thereof to a hydrolysis reaction using hydrazine and/or an acid.

This reaction can be performed by the method described in Courses in Experimental Chemistry, 4th edition, Vol. 20, pp. 284~292, 1992, MARUZEN, for example.

In Manufacturing method B, in a case where the compound represented by General Formula [1] or a salt thereof is reacted with the compound represented by General Formula [2], in which at least one of $R^2$ or $R^3$ is an amino-protecting group, or a salt thereof or with hexamethylenetetramine, the obtained compound or a salt thereof can be subjected to a deprotection reaction or a hydrolysis reaction.

As Manufacturing method B, Manufacturing method (1a), Manufacturing (1b), and Manufacturing method (1c) are preferable; Manufacturing method (1b) is more preferable; Manufacturing method (1b) using the compound represented by General Formula [2b], in which $R^{2a}$ is a $C_{3-6}$ alkoxycarbonyl group and $R^{3a}$ is a $C_{3-6}$ alkoxycarbonyl group, or a salt thereof is more preferable; and Manufacturing method (1b) using di(tert-butoxycarbonyl)amine is particularly preferable.

In a case where di(tert-butoxycarbonyl)amine is used, the compound represented by General Formula [3b] or a salt thereof having high purity can be manufactured by a simple operation with high yield. Furthermore, the reaction time can be shortened, and the reaction can be performed at a lower temperature.

The compound represented by General Formula [3b] or a salt thereof has high bulk density, and it is easy to handle the compound or a salt thereof.

Furthermore, in a case where the compound represented by General Formula [3b] or a salt thereof is used, the compound represented by General Formula [5] or a salt thereof having high purity can be manufactured by a simple operation with high yield.

An example of the manufacturing method of the present invention will be shown below.

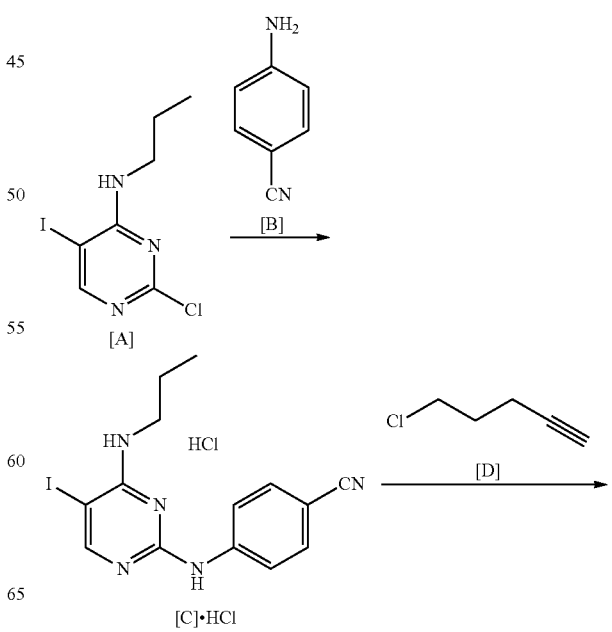

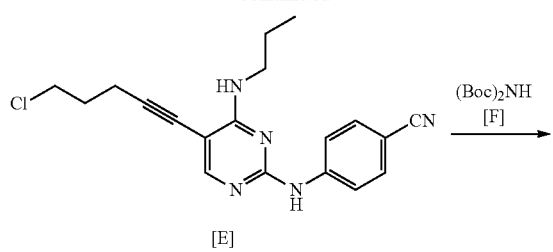

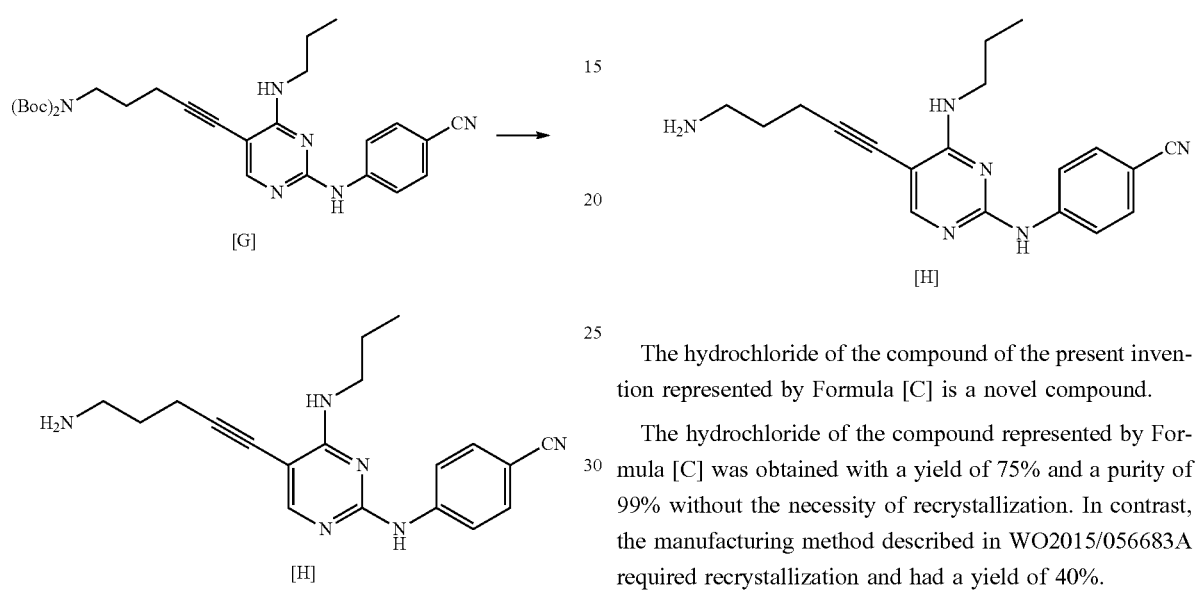

The manufacturing method shown below is described in WO2015/056683A.

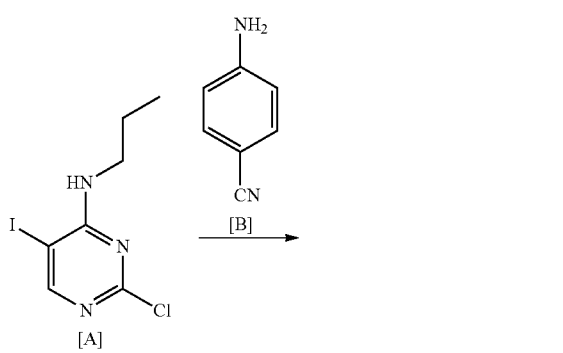

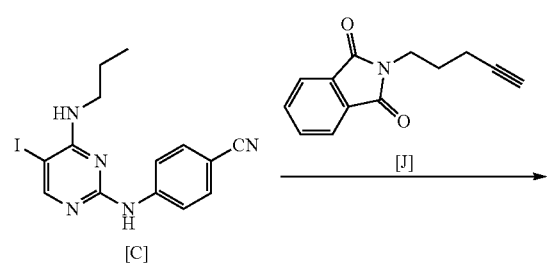

The hydrochloride of the compound of the present invention represented by Formula [C] is a novel compound.

The hydrochloride of the compound represented by Formula [C] was obtained with a yield of 75% and a purity of 99% without the necessity of recrystallization. In contrast, the manufacturing method described in WO2015/056683A required recrystallization and had a yield of 40%.

The manufacturing method of the present invention is better than the manufacturing method described in WO2015/056683A.

The hydrochloride of the compound represented by Formula [C] is a useful compound.

The compound of the present invention represented by Formula [E] is a novel compound.

By using the compound represented by Formula [D] instead of the compound represented by Formula [J], the amount of the palladium catalyst and the copper(I) iodide used was greatly reduced. As a result, the amount of a metal remaining in the compound represented by Formula [E] was significantly reduced.

The compound represented by Formula [D] is cheaper than the compound represented by Formula [J] and is easily obtained.

The manufacturing method of the present invention is better than the manufacturing method described in WO2015/056683A.

The manufacturing method using the compound represented by Formula [D] is useful.

The compound represented by Formula [E] and the compound represented by Formula [G] are useful compounds.

[Manufacturing Method C]

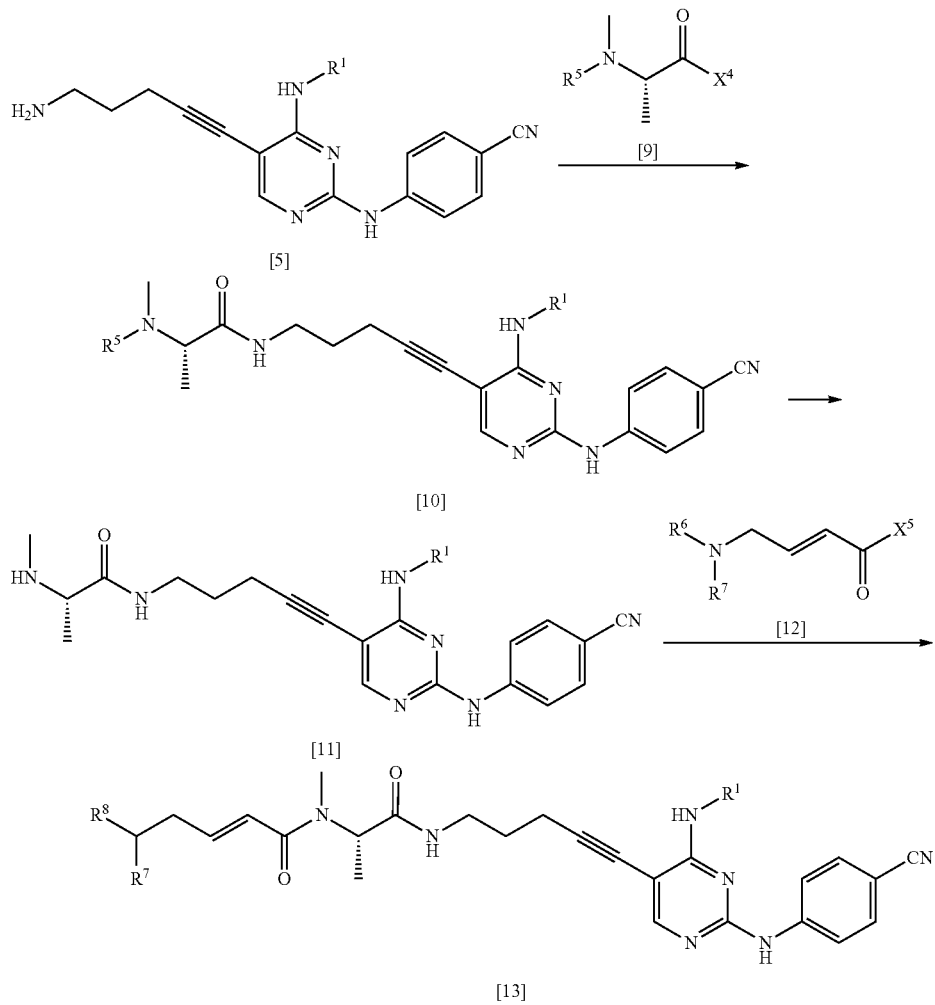

(In the formula, $R^1$, $R^5$, $R^6$, $R^7$, $X^4$, and $X^5$ have the same definition as described above.)

<First Step>

(1a) Case where $X^4$ is Hydroxyl Group

As the compound represented by General Formula [9], for example, N-(tert-butoxycarbonyl)-N-methyl-L-alanine is known.

The compound represented by General Formula [10] or a salt thereof can be manufactured by reacting the compound represented by General Formula [5] or a salt thereof with the compound represented by General Formula [9] or a salt thereof in the presence of a condensing agent or an acid halide and a base.

This reaction can be performed by the methods described in, for example, Chemical Reviews, Vol. 97, p. 2243, 1997, Chemical Synthesis of Natural Product Peptides: Coupling Methods for the Incorporation of Noncoded Amino Acids into Peptides or Tetrahedron, 2004, Vol. 60, p. 2447, Recent development of peptide coupling reagents in organic synthesis.

The solvent used in this reaction is not particularly limited as long as the solvent does not affect the reaction. Examples of the solvent include halogenated hydrocarbons, ethers, esters, amides, nitriles, sulfoxides, and aromatic hydrocarbons. These solvents may be used by being mixed together.

Examples of preferred solvents include amides. Among these, N,N-dimethylformamide or N-methylpyrrolidone is more preferable.

The amount of the solvent used is not particularly limited, and may be 1 to 500 times (v/w) the amount of the compound represented by General Formula [5] or a salt thereof.

Examples of the base used in this reaction include inorganic bases and organic bases.

Examples of preferred bases include organic bases. Among these, triethylamine, N,N-diisopropylethylamine, and 4-methylmorpholine are more preferable, and N,N-diisopropylethylamine and 4-methylmorpholine are even more preferable.

The amount of the base used may be 1 to 50 times and preferably 1 to 10 times the amount of the compound represented by General Formula [5] or a salt thereof in terms of mole.

Examples of the condensing agent used in this reaction include carbodiimides such as N,N'-diisopropylcarbodiimide (DIC), N,N'-di-(tert-butyl)carbodiimide, N,N'-dicyclohexylcarbodiimide (DCC), N-(tert-butyl)-N'-ethylcarbodiimide (BEC), N-cyclohexyl-N'-(2-morpholinoethyl)carbodiimide (CMC), and 1-ethyl-3-(3-dimethylaminopropyl)carbodiimide (EDC); imidazoliums such as 1,1'-carbonyldiimidazole (CDI) and 1,1'-carbonyldi(1,2,4-triazole) (CDT); acid azides such as diphenylphosphoryl azide; acid cyanides such as diethylphosphoryl cyanide; 2-ethoxy-1-ethoxycarbonyl-1,2-dihydroxyquinoline; and uroniums such as O-(benzotriazol-1-yl)-N,N,N',N'-tetramethyluronium hexafluorophosphate (HBTU), O-(7-azabenzotriazol-1-yl)-N,N,N',N'-tetramethyluronium hexafluorophosphate (HATU), O-(benzotriazol-1-yl)-N,N,N',N'-bis(tetramethylene)uronium hexafluorophosphate (HIBPyU), O-(benzotriazol-1-yl)-N,N,N',N'-bis(pentamethylene)uronium hexafluorophosphate (HIBPipU), O-(6-chlorobenzotriazol-l-yl)-N,N,N',N'-tetramethyluronium hexafluorophosphate (HCTU), O-(3,4-dihydro-4-oxo-1,2,3-benzotriazin-3-yl)-N,N,N',N'-tetramethyluronium hexafluorophosphate (HDBTU), O-(2-oxo-1 (2H)pyridyl)-N,N,N',N'-tetramethyluronium hexafluorophosphate (TPTTJ), O-((ethoxycarbonyl)cyanomethyleneamino)-N,N,N',N'-tetramethyluronium hexafluorophosphate (HOTU), O-((ethoxycarbonyl)cyanomethyleneamino)-N,N,N',N'-tetramethyluronium tetrafluoroborate (TOTU), N,N,N',N'-tetramethyl-O—(N-succinimidyl)uronium hexatluorophosphate (HSTU), N,N,N',N'-tetramethyl-O—(N-succinimidyl)uronium tetrafluoroborate (TSTIU) dipyrrolidino(N-succinimidyloxy)carbenium hexafluorophosphate (HSPyU), and S-(1-oxide-2-pyridyl)-N,N,N',N'-tetramethyluronium tetrafluoroborate (TOTT).

Examples of preferred condensing agents include carbodiimides, and among these, EDC is more preferable.

The amount of the condensing agent used may be 1 to 50 times and preferably 1 to 5 times the amount of the compound represented by General Formula [5] or a salt thereof in terms of mole.

In a case where carbodiimides are used as a condensing agent, it is preferable to add additives.

Examples of the additives include 1-hydroxybenzotriazole (HOBT), 1-hydroxy-7-azabenzotriazole (HOAT), and ethyl(hydroxyimino)cyanoacetate. Among these, HOBT and ethyl(hydroxyimino)cyanoacetate are preferable.

The amount of the additives used may be 0.01 to 10 times and preferably 0.1 to 1 time the amount of the compound represented by General Formula [5] or a salt thereof in terms of mole.

Examples of the acid halide used in this reaction include carboxylic acid halides such as acetyl chloride and trifluoroacetyl; sulfonic acid halides such as methanesulfonyl chloride and tosyl chloride; and chloroformic acid esters such as ethyl chloroformate and isobutyl chloroformate.

The amount of the compound represented by General Formula [9] or a salt thereof used is not particularly limited, and may be 1 to 10 times the amount of the compound represented by General Formula [5] or a salt thereof in terms of mole.

This reaction may be performed for 30 minutes to 48 hours at a temperature of −30° C. to 150° C. and preferably at a temperature of 0° C. to 100° C.

(1b) Case where $X^4$ is Leaving Group

The compound represented by General Formula [10] or a salt thereof can be manufactured by reacting the compound represented by General Formula [5] or a salt thereof with the compound represented by General Formula [9] in the presence of a base.

The solvent used in this reaction is not particularly limited as long as the solvent does not affect the reaction. Examples of the solvent include halogenated hydrocarbons, ethers, esters, amides, nitriles, and aromatic hydrocarbons. These solvents may be used by being mixed together.

The amount of the solvent used is not particularly limited, and may be 1 to 500 times (v/w) the amount of the compound represented by General Formula [5] or a salt thereof.

Examples of the base used in this reaction include inorganic bases and organic bases.

The amount of the base used may be 1 to 50 times and preferably 1 to 5 times the amount of the compound represented by General Formula [5] or a salt thereof in terms of mole.

The amount of the compound represented by General Formula [9] or a salt thereof used is not particularly limited, and may be 1 to 10 times the amount of the compound represented by General Formula [5] or a salt thereof in terms of mole.

This reaction may be performed for 30 minutes to 48 hours at a temperature of −30° C. to 150° C. and preferably at a temperature of 0° C. to 100° C.

As the first step, Manufacturing method (1a) is preferable, and a manufacturing method using N-(tert-butoxycarbonyl)-N-methyl-L-alanine is more preferable.

<Second Step>

The compound represented by General Formula [11] or a salt thereof can be manufactured by deprotecting the compound represented by General Formula [10] or a salt thereof.

This reaction can be performed by the method described in, for example, Greene's Protective Groups in Organic Synthesis, $5^{th}$ edition, pp. 895~1193, 2014, John Wiley & Sons, INC.

<Third Step>

The compound represented by General Formula [13] or a salt thereof can be manufactured by reacting the compound represented by General Formula [11] or a salt thereof with the compound represented by General Formula [12] or a salt thereof in the presence of a base and a condensing agent or an acid halide.

This reaction may be performed based on <First step> of Manufacturing method C.

In a case where the compounds used in the aforementioned manufacturing methods include a solvate, a hydrate, and crystals of various shapes, these solvate, hydrate, and crystals of various shapes can also be used.

Among the compounds used in the aforementioned manufacturing methods, for example, for the compound having an amino group, a hydroxyl group, a carboxyl group, and the like, these groups can be protected in advance with general protecting groups, and after the reaction, these protecting groups can be deprotected by a conventionally known method.

The compounds obtained by the aforementioned manufacturing methods can be induced to become other compounds by being subjected to a conventionally known reaction such as condensation, addition, oxidation, reduction, transition, substitution, halogenation, dehydration, or hydrolysis or by combining these reactions appropriately, for example.

EXAMPLES

Hereinafter, the present invention will be described based on reference examples and examples, but the present invention is not limited thereto.

As a support in silica gel column chromatography, SILICA GEL 60 (spherical) (KANTO KAGAKU) was used.

The mixing ratio in an eluent is volume ratio.

The $^1$H-NMR spectrum was measured using JNM-AL400 (JEOL Ltd.) by using tetramethylsilane as an internal standard.

The MS spectrum was measured using LCMS-2020 (Shimadzu Corporation).

The meanings of the following abbreviations are as below.
Boc: tert-butoxycarbonyl
Ms: methylsulfonyl
Pr: propyl Reference Example 1

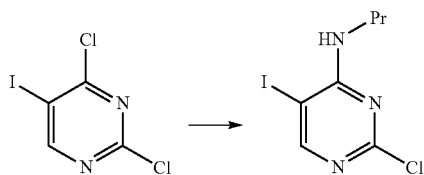

While being cooled with ice, 3.55 mL of propylamine was added to 83 mL of a tetrahydrofuran solution containing 5.77 g of 2,4-dichloro-5-iodopyrimidine synthesized according to the method described in WO2008/155140A1 and 7.86 mL of N,N-diisopropylethylamine, and the mixture was stirred for 1 hour at room temperature. Then, water and ethyl acetate were added to the reaction mixture. The organic layer was fractionated, and the water layer was extracted using ethyl acetate. The organic layer and the extract were mixed together, washed sequentially with a 1.0 mol/L aqueous hydrochloric acid solution, water, a saturated aqueous sodium hydrogen carbonate solution, and a saturated aqueous sodium chloride solution, and then dried over anhydrous magnesium sulfate. The solvent was distilled away under reduced pressure, thereby obtaining 6.44 g of 2-chloro-5-iodo-N-propylpyrimidin-4-amine in the form of oil.

MS m/z (M+H): 298.3

Reference Example 2

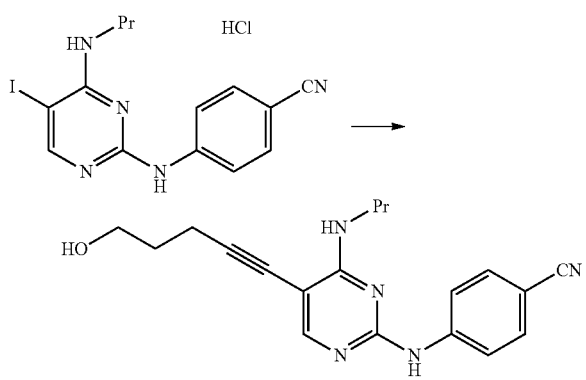

In a nitrogen atmosphere, 11.0 g of triethylamine, 0.17 g of bis(triphenylphosphine)palladium(II) dichloride and 0.23 g of copper(I) iodide were added to mL of a tetrahydrofuran suspension containing 5.00 g of N$^2$-(4-cyanophenyl)-5-iodo-N$^4$-propylpyrimidine-2,4-diamine hydrochloride, 1.32 g of 4-pentyn-1-ol was added thereto at a temperature of 40° C. to 45° C., and the mixture was stirred for 4 hours and 30 minutes at the same temperature. The reaction mixture was cooled to 30° C., and 25 mL of a 15% aqueous ammonium chloride solution was added thereto. The organic layer was fractionated and washed with a 15% aqueous ammonium chloride solution. Then, 0.25 g of N-acetyl-L-cysteine was added thereto, and the mixture was stirred for 30 minutes at a temperature of 20° C. to 30° C. 7.5 mL of tetrahydrofuran and 50 mL of methanol were added to the reaction mixture, and the mixture was stirred for 30 minutes at a temperature of 20° C. to 30° C. 50 mL of water was added to the reaction mixture, and the mixture was stirred for 30 minutes at a temperature of 20° C. to 30° C. and then stirred for 1 hour at a temperature of 0° C. to 10° C. The solid content was collected by filtration, thereby obtaining 3.06 g of 4-((5-(5-hydroxy-1-pentyn-1-yl)-4-(propylamino)pyrimidin-2-yl)amino)benzonitrile as a pale yellow solid.

$^1$H-NMR (CDCl$_3$) δ: 8.00 (1H, s), 7.75 (2H, d, J=8.8 Hz), 7.57 (2H, d, J=8.8 Hz), 7.17 (1H, brs), 5.69 (2H, t, J=5.2 Hz), 3.84 (2H, t, J=5.8 Hz), 3.50-3.42 (2H, m), 2.62 (2H, t, J=7.01 Hz), 1.93-1.84 (2H, m), 1.75-1.64 (2H, m), 1.02 (3H, t, J=7.6 Hz).

Example 1

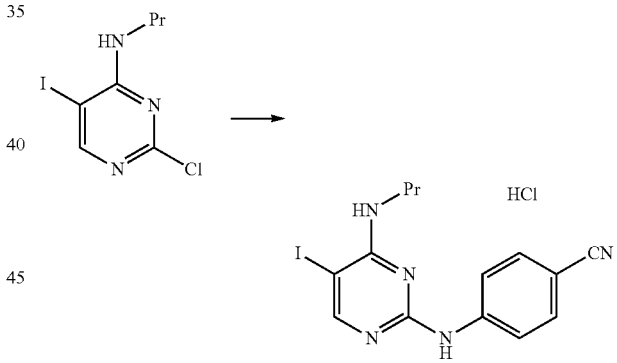

At room temperature, 49.6 g of 4-aminobenzonitrile and 36 mL of hydrochloric acid were added to 125 mL of a N-methylpyrrolidone solution containing 31.3 g of 2-chloro-5-iodo-N-propylpyrimidin-4-amine, and the mixture was stirred for 5 hours at a temperature of 50° C. to 60° C. The reaction mixture was cooled to 30° C., 250 mL of methanol was then added thereto, and the mixture was stirred for 30 minutes at 30° C. 250 mL of water was added to the reaction mixture, and the mixture was stirred for 1 hour at 28° C. The solid content was collected by filtration, thereby obtaining 32.9 g of N$^2$-(4-cyanophenyl)-5-iodo-N$^4$-propylpyrimidine-2,4-diamine hydrochloride as a pale yellow solid.

$^1$H-NMR (DMSO$_6$) δ: 10.28 (1H, brs), 8.25 (1H, s), 7.87 (2H, d, J=8.8 Hz), 7.76 (2H, d, J=8.8 Hz), 7.56 (1H, brs), 3.38 (2H, dd, J=6.0, 14.3 Hz), 1.65-1.53 (2H, m), 0.90 (3H, t, J=7.4 Hz).

Example 2

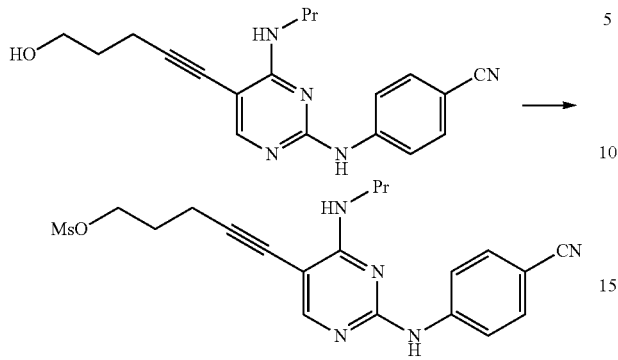

At 10° C., 0.23 g of triethylamine and 0.20 g of methanesulfonyl chloride were added to 5.0 mL of chloroform suspension containing 0.50 g of 4-((5-(5-hydroxy-1-pentyn-1-yl)-4-(propylamino)pyrimidin-2-yl)amino)benzonitrile, and the mixture was stirred for 3 hours at a temperature of 0° C. to 10° C. 0.06 g of triethylamine and 0.05 g of methanesulfonyl chloride were added to the reaction mixture, and the mixture was stirred for 3 hours at a temperature of 0° C. to 10° C. 0.06 g of triethylamine and 0.05 g of methanesulfonyl chloride were added to the reaction mixture, and the mixture was stirred for 1 hour at a temperature of 0° C. to 10° C. Water and chloroform were added to the reaction mixture. The organic layer was fractionated and dried over anhydrous magnesium sulfate, and then the solvent was distilled away under reduced pressure, thereby obtaining 0.62 g of (5-(2-(4-cyanoanilino)-4-(propylamino)pyrimidin-5-yl)-4-pentyn-1-yl)methane sulfonate as a pale yellow solid.

$^1$H-NMR (CDCl$_3$) δ: 7.98 (1H, s), 7.76 (2H, d, J=9.2 Hz), 7.57 (2H, d, J=9.2 Hz), 7.54 (1H, brs), 5.86 (2H, t, J=5.2 Hz), 4.44 (2H, t, J=5.6 Hz), 3.51-3.42 (2H, m), 3.06 (3H, s), 2.68 (2H, t, J=6.6 Hz), 2.08-2.00 (2H, m), 1.74-1.65 (2H, m), 1.01 (3H, t, J=7.4 Hz).

Example 3

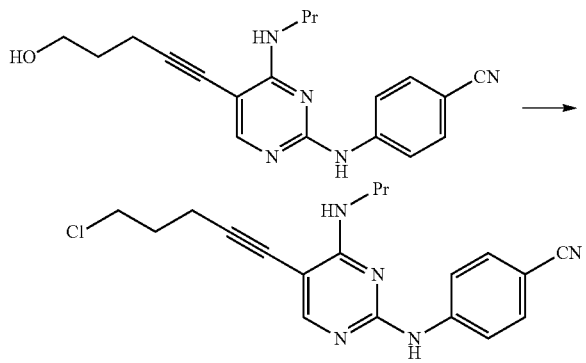

0.53 g of thionyl chloride was added to 5.0 mL of a toluene suspension containing 0.50 g of 4-((5-(5-hydroxy-1-pentyn-1-yl)-4-(propylamino)pyrimidin-2-yl)amino)benzonitrile, and the mixture was stirred for 3 hours at 80° C. The reaction mixture was cooled to 20° C., and then tetrahydrofuran and a 5% aqueous sodium hydrogen carbonate solution were added thereto. The organic layer was fractionated and dried over anhydrous magnesium sulfate, and then the solvent was distilled away under reduced pressure, thereby obtaining 0.47 g of 4-((5-(5-chloro-1-pentyn-1-yl)-4-(propylamino)pyrimidin-2-yl)amino)benzonitrile as a yellowish brown solid.

$^1$H-NMR (CDCl$_3$) δ: 8.01 (1H, s), 7.75 (2H, d, J=9.0 Hz), 7.57 (2H, d, J=9.0 Hz), 7.25 (1H, brs), 5.58 (2H, t, J=5.4 Hz), 3.72 (2H, t, J=6.2 Hz), 3.52-3.42 (2H, m), 2.70 (2H, t, J=6.8 Hz), 2.12-2.03 (2H, m), 1.76-1.65 (2H, m), 1.02 (3H, t, J=7.4 Hz).

Example 4

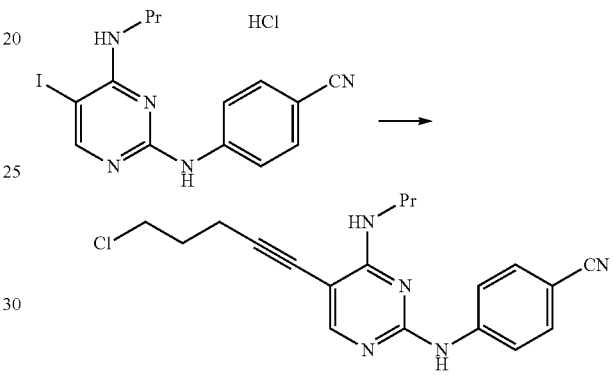

In a nitrogen atmosphere, 132 g of triethylamine, 2.0 g of bis(triphenylphosphine)palladium(II) dichloride, and 2.8 g of copper(I) iodide were added to 480 mL of a tetrahydrofuran suspension containing 60.0 g of N$^2$-(4-cyanophenyl)-5-iodo-N$^4$-propylpyrimidine-2,4-diamine hydrochloride, 19.3 g of 5-chloro-1-pentyne was added thereto at 30° C., and the mixture was stirred for 1 hour at the same temperature. The reaction mixture was cooled to 25° C., 30 mL of tributylphosphine was added thereto, and the mixture was stirred for 2 hours at a temperature of 20° C. to 30° C. 300 mL of a 15% aqueous ammonium chloride solution was added to the reaction mixture.

The organic layer was fractionated and washed twice with 300 mL of a 15% aqueous ammonium chloride solution. Then, 600 mL of methanol was added thereto, and the mixture was stirred for 1 hour at a temperature of 20° C. to 30° C. 300 mL of water was added to the reaction mixture, and the mixture was stirred for 30 minutes at a temperature of 20° C. to 30° C. and then stirred for 1 hour at a temperature of 0° C. to 10° C. The solid content was collected by filtration, thereby obtaining 45.8 g of 4-((5-(5-chloro-1-pentyn-1-yl)-4-(propylamino)pyrimidin-2-yl)amino)benzonitrile as a pale yellow solid.

As a result of measuring the amount of residual metals, it was confirmed that the amount of palladium was equal to or smaller than 50 ppm, and the amount of copper was equal to or smaller than 50 ppm.

$^1$H-NMR (DMSO$_6$) δ: 9.80 (1H, s), 8.01 (1H, s), 7.96 (2H, d, J=8.8 Hz), 7.68 (2H, d, J=8.8 Hz), 6.94 (1H, t, J=6.5 Hz), 3.77 (2H, t, J=6.5 Hz), 3.43-3.35 (2H, m), 2.62 (2H, t, J=7.1 Hz), 2.07-1.98 (2H, m), 1.67-1.54 (2H, m), 0.92 (3H, t, J=7.5 Hz).

Example 5

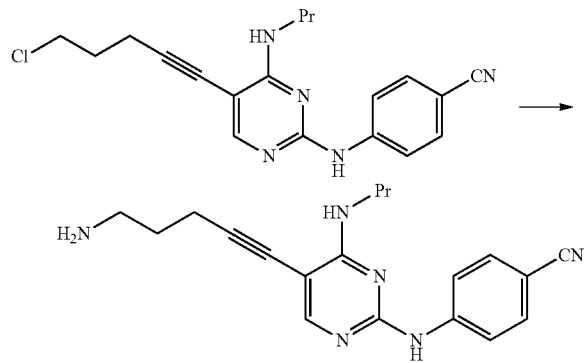

2.5 mL of N,N-diisopropylethylamine and 2.05 g of ammonium iodide were added to 5.0 mL of a N,N-dimethylacetamide suspension containing 0.50 g of 4-((5-(5-chloro-1-pentyn-1-yl)-4-(propylamino)pyrimidin-2-yl)amino)benzonitrile, and the mixture was stirred for 27 hours at 50° C. The reaction mixture was cooled to room temperature, and then 20 mL of ethyl acetate and 40 mL of water were added thereto. The solid content was collected by filtration, 20 mL of 2-butanone and 20 mL of water were added thereto, and a 25% aqueous sodium hydroxide solution was added thereto such that the pH thereof was adjusted and became 13.5. The organic layer was fractionated, and the solvent was distilled away under reduced pressure. The obtained residue was purified by silica gel column chromatography (eluent: chloroform/methanol=5/1→3/1→2/1), thereby obtaining 0.11 g of 4-((5-(5-amino-1-pentyn-1-yl)-4-(propylamino)pyrimidin-2-yl)amino)benzonitrile as a pale yellow solid.

$^1$H-NMR (DMSO$_6$) δ: 9.78 (1H, s), 7.97 (1H, s), 7.96 (2H, d, J=8.6 Hz), 7.68 (2H, d, J=8.6 Hz), 7.09-6.99 (1H, m), 3.42-3.27 (2H, m), 2.67 (2H, d, J=6.6 Hz), 2.54-2.47 (2H, m), 1.72-1.54 (4H, m), 0.92 (3H, t, J=7.4 Hz).

Example 6

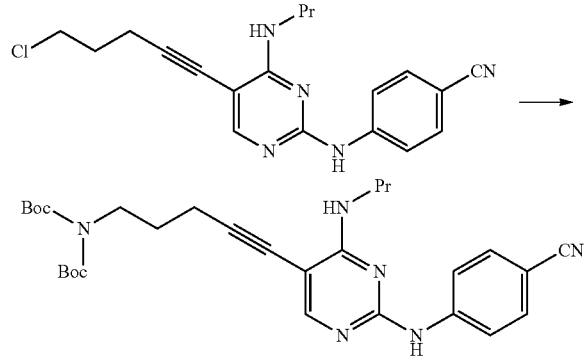

135 mL of a N-methyl-2-pyrrolidone suspension containing 45.0 g of 4-((5-(5-chloro-1-pentyn-1-yl)-4-(propylamino)pyrimidin-2-yl)amino)benzonitrile, 41.4 g of di(tert-butoxycarbonyl)amine, and 70.3 g of potassium carbonate was stirred for 6 hours and 15 minutes at 70° C. The reaction mixture was cooled to room temperature and then left to stand overnight. The reaction mixture was heated to 55° C., and 315 mL of 2-butanone and 180 mL water were added thereto. The organic layer was fractionated, washed with a 10% aqueous sodium chloride solution, and then cooled to 40° C., followed by stirring for 2 hours at a temperature of 35° C. to 40° C. The reaction mixture was cooled to 25° C., 315 mL of a 50% aqueous methanol solution was then added thereto, and the mixture was stirred for 3 hours and 30 minutes at a temperature of 15° C. to 25° C. The solid content was collected by filtration, thereby obtaining 63.5 g of tert-butyl-N-(tert-butoxycarbonyl)-N-(5-(2-(4-cyanoanilino)-4-(propylamino)pyrimidin-5-yl)-4-pentyn-1-yl)carbamate.

$^1$H-NMR (DMSO-d$_6$) δ: 9.80 (1H, s), 8.00 (1H, s), 7.96 (2H, d, J=8.6 Hz), 7.68 (2H, d, J=8.6 Hz), 6.94 (1H, t, J=6.0 Hz), 3.65 (2H, t, J=7.11 Hz), 3.45-3.36 (2H, m), 2.49-2.44 (2H, m), 1.83-1.73 (2H, m), 1.67-1.56 (2H, m), 1.45 (18H, s), 0.92 (3H, t, J=7.3 Hz).

Example 7

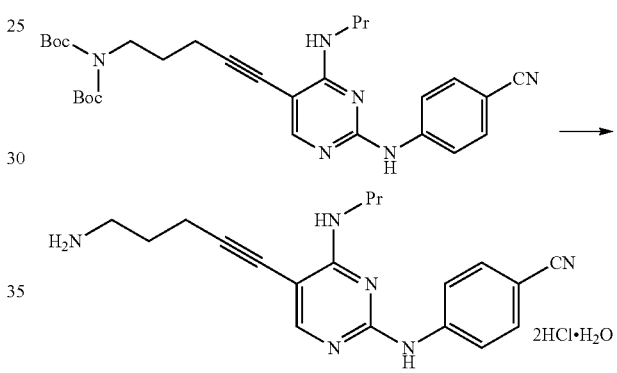

At a temperature of 40° C. to 45° C., 540 mL of a 2-butanone solution containing 60.0 g of tert-butyl-N-(tert-butoxycarbonyl)-N-(5-(2-(4-cyanoanilino)-4-(propylamino)pyrimidin-5-yl)-4-pentyn-1-yl)carbamate was added to a mixed solution of 111 g of 37% hydrochloric acid, 240 mL, of acetonitrile, and 300 mL of water. 60 mL of 2-butanone was added to the obtained mixture, and then the mixture was stirred for 6 hours at the same temperature and left to stand overnight at room temperature. The reaction mixture was heated to 45° C., and 180 mL of a 25% aqueous sodium hydroxide solution was added thereto. The organic layer was fractionated and washed sequentially with 30 mL of water and 60 mL of acetonitrile at 60° C., and 33.2 g of 37% hydrochloric acid was added thereto, followed by stirring for 2 hours at a temperature of 55° C. to 65° C. 300 mL of 2-butanone was added to the reaction mixture, and then the mixture was stirred for 2 hours at a temperature of 0° C. to 10° C. The solid content was collected by filtration, thereby obtaining 43.9 g of 4-((5-(S-amino-1-pentyn-1-yl)-4-(propylamino)pyrimidin-2-yl)amino)benzonitrile dihydrochloride monohydrate as a white solid.

$^1$H-NMR (DMSO-d$_6$) δ: 10.64 (1H, brs), 8.10 (1H, s), 8.03 (3H, brs), 7.89 (2H, d, J=8.8 Hz), 7.79 (2H, d, J=8.8 Hz), 3.42 (2H, dd, J=6.6, 14.4 Hz), 2.97-2.85 (2H, m), 2.62 (2H, d, J=7.0 Hz), 1.92-1.77 (2H, m), 1.67-1.54 (2H, m), 0.92 (3H, t, J=7.5 Hz).

Example 8

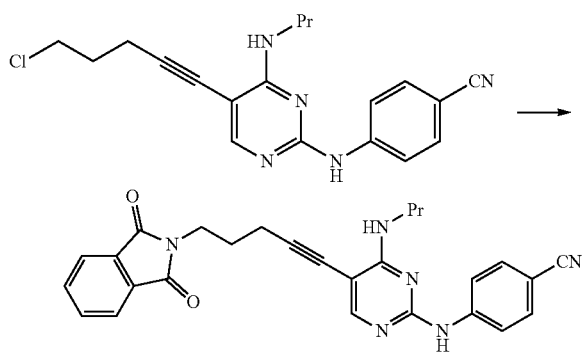

A suspension of 1.00 g of 4-((5-(5-chloro-1-pentyn-1-yl)-4-(propylamino)pyrimidin-2-yl)amino)benzonitrile, 6 mL of dimethylsulfoxide, 0.68 g of potassium phthalimide, and 0.38 g of lithium iodide was stirred for 19 hours at 40° C. At the same temperature, 10 mL of a 50% aqueous 2-propanol solution was added thereto, and the mixture was cooled to room temperature. The solid content was collected by filtration, thereby obtaining 1.12 g of 4-((5-(5-(1,3-dioxoisoindolin-2-yl)-1-pentyn-1-yl)-4-(propylamino)pyrimidin-2-yl)amino)benzonitrile as a pale yellow solid.

$^1$H-NMR (DMSO-$d_6$) δ: 9.79 (1H, s), 7.96 (2H, d, J=8.8 Hz), 7.89-7.84 (2H, m), 7.84-7.79 (2H, m), 7.77 (1H, s), 7.68 (2H, d, J=8.8 Hz), 6.95 (3H, t, J=6.0 Hz), 3.75 (3H, t, J=6.6 Hz), 3.45-3.25 (2H, m), 2.55-2.46 (2H, m), 1.96-1.85 (2H, m), 1.68-1.56 (2H, m), 0.93 (3H, t, J=7.4 Hz).

Example 9

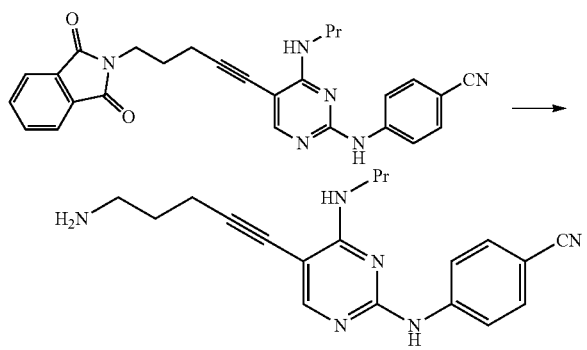

2.5 mL of an ethylenediamine solution containing 0.50 g of 4-((5-(5-(1,3-dioxoisoindolin-2-yl)-1 pentyn-1-yl)-4-(propylamino)pyrimidin-2-yl)amino)benzonitrile was stirred for 3 hours at a temperature of 80° C. to 90° C. The reaction mixture was cooled to room temperature, 0.2 mL of water was added thereto, and the mixture was stirred for 4 hours at the same temperature. 10 mL of water was added to the reaction mixture, and the mixture was stirred for 30 minutes at room temperature. The solid content was collected by filtration, thereby obtaining 0.31 g of 4-((5-(5-amino-1-pentyn-1-yl)-4-(propylamino)pyrimidin-2-yl)amino)benzonitrile as a pale yellow solid.

MS m/z (M−H): 333

$^1$H-NMR (DMSO-$d_6$) δ: 9.78 (1H, s), 8.00-7.93 (3H, m), 7.71-7.65 (2H, m), 7.11-6.99 (1H, m), 3.55-3.15 (2H, m), 3.09 (1H, dd, J=6.6, 12.2 Hz), 2.66 (2H, t, J=6.6 Hz), 2.53-2.43 (2H, m), 1.70-1.54 (4H, m), 0.92 (3H, t, J=7.4 Hz).

Example 10

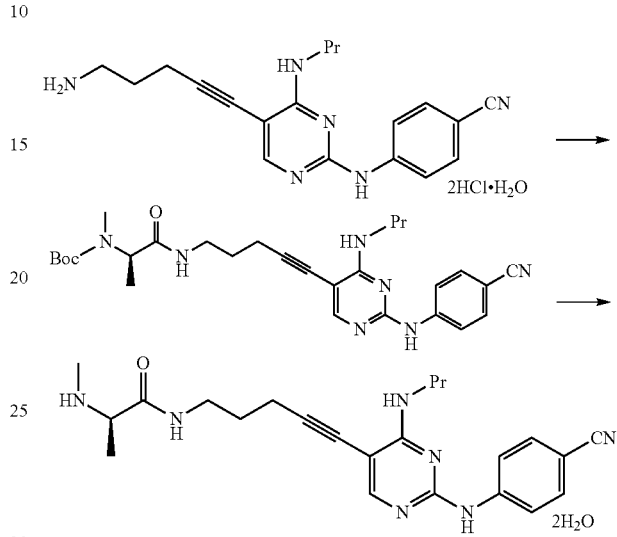

40.0 g of 4-((5-(5-amino-1-pentyn-1-yl)-4-(propylamino)pyrimidin-2-yl)amino)benzonitrile dihydrochloride monohydrate, 22.9 g of N-(tert-butoxycarbonyl)-N-methyl-L-alanine, 2.88 g of 1-hydroxybenzotriazole monohydrate, and 21.6 g of 1-ethyl-3-(3-dimethylaminopropyl)carbodiimide hydrochloride were sequentially added to 160 mL of a N-methyl-2-pyrrolidone solution containing 43.8 g of N,N-diisopropylethylamine, and the mixture was stirred for 7 hours and 30 minutes at a temperature of 20° C. to 30° C. 200 mL of 2-methyltetrahydrofuran was added to the reaction mixture, and then 200 mL of a 10% aqueous sodium chloride solution and 43.4 mL of a 25% aqueous sodium hydroxide solution were sequentially added thereto. The organic layer was fractionated, 200 mL of a 10% aqueous citric acid solution was added thereto, and then 28.0 mL of acetic acid was added thereto. The organic layer was fractionated and washed with a 10% aqueous sodium chloride solution.

80 mL of water was added to the obtained organic layer, 74.1 g of 37% hydrochloric acid was then added thereto at 40° C., and the mixture was stirred for 4 hours and 30 minutes at the same temperature. 280 mL of water was added to the reaction mixture, the mixture was cooled to 30° C., and then 116 mL of a 25% aqueous sodium hydroxide solution was added thereto. The mixture was stirred for 1 hour at a temperature of 20° C. to 30° C., then cooled to 10° C., and stirred for 5 hours at the same temperature. The solid content was collected by filtration, thereby obtaining 41.1 g of (S)—N-(5-(2-((4-cyanophenyl)amino)-4-(propylamino)pyrimidin-5-yl)-4-pentyn-1-yl)-2-(methylamino)propanamide dihydrate as a pale yellow solid.

$^1$H-NMR (DMSO-$d_6$) δ: 9.78 (1H, s), 8.00-7.94 (3H, m), 7.92 (1H, t, J=6.0 Hz), 7.68 (2H, d, J=8.8 Hz), 7.20 (1H, t, J=5.6 Hz), 3.45-3.37 (2H, m), 3.29-3.23 (2H, m), 2.98-2.88 (1H, m), 2.45 (2H, t, J=7.0 Hz), 2.20 (3H, s), 1.89 (1H, brs), 1.74-1.55 (4H, m), 1.11 (3H, d, J=6.8 Hz), 0.92 (3H, t, J=7.5 Hz).

Example 11

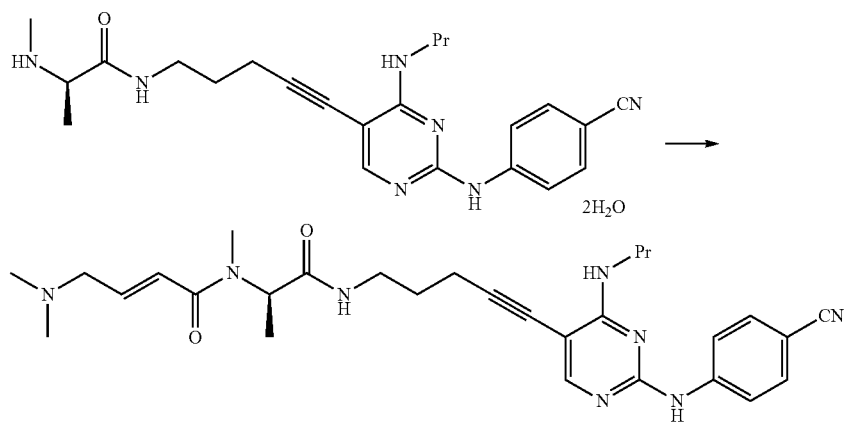

25.3 g of 1-ethyl-3-(3-dimethylaminopropyl)carbodiimide hydrochloride, 18.7 g of ethyl(hydroxyimino)cyanoacetate, and 40.0 g of 4-methylmorpholine were sequentially added to 200 mL of N,N-dimethylacetamide, and then the mixture was cooled to 10° C. 40.0 g of (S)—N-(5-(2-((4-cyanophenyl)amino)-4-(propylamino)pyrimidin-5-yl)-4-pentyn-1-yl)-2-(meth ylamino)propanamide dihydrate and 21.8 g of 4-dimethylaminocrotonic acid hydrochloride were added to the mixture, and the mixture was stirred for 5 hours and 45 minutes at a temperature of 10° C. to 15° C. 400 mL of 4-methyl-2-pentanone was added to the reaction mixture, and then 400 mL of a 15% aqueous sodium chloride solution was added thereto. The reaction mixture was left to stand overnight at room temperature, 48 mL of a 25% aqueous sodium hydroxide solution was then added thereto, and the mixture was stirred for 20 minutes at a temperature of 30° C. to 40° C. The organic layer was fractionated and washed with a 10% aqueous sodium chloride solution. 400 mL of water and 17.2 mL of acetic acid were sequentially added to the obtained organic layer. The water layer was fractionated, 400 mL of methanol was added thereto, and the mixture was cooled to 30° C. Then, 35.1 mL of a 25% aqueous sodium hydroxide solution was added thereto, and the mixture was stirred for 2 hours at a temperature of 20° C. to 30° C. The reaction mixture was cooled to 10° C. and stirred for 2 hours at a temperature of 0° C. to 10° C. The solid content was collected by filtration, thereby obtaining 43.1 g of (S,E)-N-(1-((5-(2-((4-cyanophenyl)amino)-4-(propylamino)pyrimidin-5-yl)-4-pentyn-1-yl)amino)-1-oxopropan-2-yl)-4-(dimethylamino)-N-methyl-2-butenamide as a pale yellow solid.

The manufacturing method of the present invention is useful as a method for industrially manufacturing a nitrogen-containing heterocyclic compound which shows excellent FLT3 inhibitory activity and is useful as an active pharmaceutical ingredient of pharmaceutical products. The compound of the present invention is useful as an intermediate used in the method for industrially manufacturing a nitrogen-containing heterocyclic compound which shows excellent FLT3 inhibitory activity and is useful as an active pharmaceutical ingredient of pharmaceutical products.

What is claimed is:

1. A compound represented by General Formula [14] or a salt thereof:

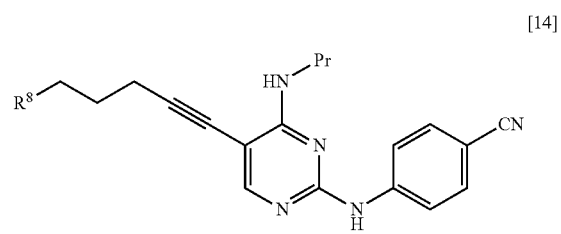

[14]

wherein in General Formula [14], $R^1$ represents a $C_{1-6}$ alkyl group which may be substituted; and $R^8$ represents a chlorine atom, a hexamethylenetetraminium group, or a group represented by General Formula [4a]:

[4a]

wherein in General Formula [4a], $R^{2a}$ represents a $C_{1-6}$ alkoxycarbonyl group; $R^{3a}$ represents a $C_{1-6}$ alkoxycarbonyl group; and * represents a binding position.

2. The compound according to claim 1 or a salt thereof, wherein $R^1$ is a $C_{2-4}$ alkyl group, and $R^8$ is a chlorine atom.

3. The compound according to claim 1 or a salt thereof, wherein $R^1$ is a $C_{2-4}$ alkyl group; and $R^8$ is a group represented by General Formula [4a]:

[4a]

wherein in General Formula [4a], $R^{2a}$ represents a $C_{1-6}$ alkoxycarbonyl group; $R^{3a}$ represents a $C_{1-6}$ alkoxycarbonyl group; and * represents a binding position.

* * * * *